(12) United States Patent
Gainer et al.

(10) Patent No.: US 10,016,384 B2
(45) Date of Patent: Jul. 10, 2018

(54) ORAL FORMULATIONS OF BIPOLAR TRANS CAROTENOIDS

(71) Applicant: Diffusion Pharmaceuticals, LLC, Charlottesville, VA (US)

(72) Inventors: John L. Gainer, Charlottesville, VA (US); Robert Murray, Charlottesville, VA (US)

(73) Assignee: DIFFUSION PHARMACEUTICALS LLC, Charlottesville, VA (US)

( * ) Notice: Subject to any disclaimer, the term of this patent is extended or adjusted under 35 U.S.C. 154(b) by 0 days.

(21) Appl. No.: 14/642,703

(22) Filed: Mar. 9, 2015

(65) Prior Publication Data

US 2015/0352068 A1    Dec. 10, 2015

Related U.S. Application Data

(63) Continuation of application No. 13/067,469, filed on Jun. 2, 2011, now Pat. No. 8,974,822.

(60) Provisional application No. 61/350,804, filed on Jun. 2, 2010.

(51) Int. Cl.
| | | |
|---|---|---|
| A61K 31/202 | (2006.01) | |
| A61K 31/724 | (2006.01) | |
| A61K 9/20 | (2006.01) | |
| A61K 9/28 | (2006.01) | |
| A61K 9/48 | (2006.01) | |

(52) U.S. Cl.
CPC ............ *A61K 31/202* (2013.01); *A61K 9/205* (2013.01); *A61K 9/2054* (2013.01); *A61K 9/2866* (2013.01); *A61K 9/4866* (2013.01); *A61K 9/4891* (2013.01); *A61K 31/724* (2013.01)

(58) Field of Classification Search
None
See application file for complete search history.

(56) References Cited

U.S. PATENT DOCUMENTS

| | | |
|---|---|---|
| 2,175,843 A | 10/1939 | Kuhn et al. |
| 2,948,748 A | 8/1960 | Guex et al. |
| 3,489,806 A | 1/1970 | Gutmann et al. |
| 3,687,990 A | 8/1972 | Gutmann et al. |
| 3,788,468 A | 1/1974 | Gainer |
| 3,853,933 A | 12/1974 | Siciliano |
| 3,853,993 A | 12/1974 | Gainer |
| 3,965,261 A | 6/1976 | Gainer |
| 3,975,519 A | 8/1976 | Gainer |
| 4,009,270 A | 2/1977 | Gainer |
| 4,038,144 A | 7/1977 | Gainer |
| 4,046,880 A | 9/1977 | Gainer |
| 4,070,460 A | 1/1978 | Gainer |
| 4,099,270 A | 7/1978 | Jabour |
| 4,105,855 A | 8/1978 | Schulz et al. |
| 4,176,179 A | 11/1979 | Gainer |
| 4,216,211 A | 8/1980 | Francis |
| 4,699,664 A | 10/1987 | Hettiarachchy et al. |
| 4,727,064 A | 2/1988 | Pitha |
| 5,032,613 A | 7/1991 | Watson |
| 5,053,240 A | 10/1991 | Todd |
| 5,107,030 A | 4/1992 | Babler |
| 5,424,407 A | 6/1995 | Tanaka et al. |
| 5,472,946 A | 12/1995 | Peck et al. |
| 5,811,119 A | 9/1998 | Mehta et al. |
| 5,817,332 A | 10/1998 | Urtti et al. |
| 6,060,511 A | 5/2000 | Gainer |
| 6,150,561 A | 11/2000 | Kreienbühl et al. |
| 6,555,526 B2 | 4/2003 | Matsuo et al. |
| 6,855,734 B2 | 2/2005 | Messadek |
| 7,145,025 B2 | 12/2006 | Lockwood et al. |
| 7,351,844 B2 | 4/2008 | Gainer et al. |
| 7,446,101 B1 | 11/2008 | Madhavi et al. |
| 7,521,584 B2 | 4/2009 | Lockwood et al. |
| 7,759,506 B2 | 7/2010 | Gainer et al. |
| 7,887,840 B2 | 2/2011 | Curatolo et al. |
| 7,919,527 B2 | 4/2011 | Gainer et al. |
| 8,017,653 B2 | 9/2011 | Gainer et al. |
| 8,030,350 B2 | 10/2011 | Gainer et al. |
| 8,206,751 B2 | 6/2012 | Gainer |
| 8,269,027 B2 | 9/2012 | Gainer et al. |
| 8,293,804 B2 | 10/2012 | Gainer |
| 8,901,174 B2 | 12/2014 | Gainer |
| 8,974,822 B2 | 3/2015 | Gainer et al. |
| 9,604,899 B2 | 3/2017 | Gainer et al. |
| 2003/0180281 A1 | 9/2003 | Bott et al. |

(Continued)

FOREIGN PATENT DOCUMENTS

| | | |
|---|---|---|
| AU | 2003215396 | 9/2003 |
| CH | 522572 | 6/1972 |

(Continued)

OTHER PUBLICATIONS

Office Action dated Apr. 12, 2016, issued in Canadian Patent Application No. 2,765,697, which is the national phase of PCT/US2010/001794.

Office Action dated May 5, 2016, issued in U.S. Appl. No. 12/801,726, which corresponds to PCT/US2010/001794.

Office Action dated Dec. 30, 2015, issued in Israeli Patent Application No. 216919, which corresponds to PCT/US2010/001794, and English translation.

Office Action dated Jan. 12, 2016, issued in Japanese Patent Application No. 2014-003614, which corresponds to PCT/US2003/026424.

Craw, M., et al., "The Characterisation of the Triplet State of Crocetin, a Water Soluble Carotenoid, by Nanosecond Laser Flash Photolyses," Photochemistry and Photobiology, 1983, vol. 38, No. 2, pp. 241-243.

(Continued)

*Primary Examiner* — Abigail Vanhorn
*Assistant Examiner* — Sarah J Chickos
(74) *Attorney, Agent, or Firm* — Hoxie & Associates LLC

(57) ABSTRACT

The subject invention relates to a variety of formulations of bipolar trans carotenoids including pharmaceutical compositions for oral delivery of a bipolar trans carotenoid comprising i) a bipolar trans carotenoid, ii) a cyclodextrin, and iii) a coating. The invention also relates to preparation of such formulations and their uses.

13 Claims, 12 Drawing Sheets

(56) References Cited

U.S. PATENT DOCUMENTS

| | | |
|---|---|---|
| 2003/0180282 A1 | 9/2003 | Serebruany et al. |
| 2003/0186931 A1 | 10/2003 | Matsuo et al. |
| 2004/0109920 A1 | 6/2004 | Reuscher et al. |
| 2004/0116729 A1 | 6/2004 | Gainer et al. |
| 2004/0162329 A1 | 8/2004 | Lockwood et al. |
| 2006/0194973 A1 | 8/2006 | Gainer et al. |
| 2006/0233877 A1 | 10/2006 | Messadek et al. |
| 2006/0276372 A1 | 12/2006 | Lockwood et al. |
| 2006/0281724 A1* | 12/2006 | Loria ............... A61K 31/57 514/178 |
| 2007/0088248 A1 | 4/2007 | Glenn et al. |
| 2007/0135521 A1 | 6/2007 | Okada et al. |
| 2007/0161610 A1 | 7/2007 | Gainer et al. |
| 2007/0166339 A1 | 7/2007 | Gupta |
| 2008/0113031 A1 | 5/2008 | Moodley et al. |
| 2008/0255246 A1 | 10/2008 | Gainer |
| 2009/0118227 A1 | 5/2009 | Jouni et al. |
| 2009/0169586 A1 | 7/2009 | Tracton |
| 2009/0176287 A1 | 7/2009 | Schmidt-Dannert et al. |
| 2010/0322918 A1 | 12/2010 | Gainer |
| 2012/0095099 A1 | 4/2012 | Gainer et al. |
| 2013/0018014 A1 | 1/2013 | Gainer |
| 2014/0051759 A1 | 2/2014 | Gainer et al. |
| 2016/0199490 A1 | 7/2016 | Gainer et al. |
| 2017/0202798 A1 | 7/2017 | Gainer et al. |

FOREIGN PATENT DOCUMENTS

| | | |
|---|---|---|
| CN | 1215723 | 5/1999 |
| CN | 1671643 A | 9/2005 |
| CN | 1708480 A | 12/2005 |
| CN | 1243120 C | 2/2006 |
| CN | 1842512 A | 10/2006 |
| CN | 1997365 | 7/2007 |
| CN | 10-1180257 | 5/2008 |
| EP | 0 612 815 A1 | 8/1994 |
| EP | 09908449 | 4/1999 |
| EP | 1 192 947 | 4/2002 |
| GB | 2 353 934 | 11/1999 |
| JP | 45-014114 | 5/1970 |
| JP | 61-254161 | 11/1986 |
| JP | 63059831 | 3/1988 |
| JP | 63-222114 A | 9/1988 |
| JP | 1-238536 | 9/1989 |
| JP | 2-121934 | 5/1990 |
| JP | A 03-056412 | 3/1991 |
| JP | A 04-264020 | 9/1992 |
| JP | 05032531 | 2/1993 |
| JP | A 05-178765 | 7/1993 |
| JP | 06-248193 | 9/1994 |
| JP | 07-023736 | 1/1995 |
| JP | 07-223960 | 8/1995 |
| JP | A 07-291854 | 11/1995 |
| JP | 09-512552 | 12/1997 |
| JP | 10-502388 A | 3/1998 |
| JP | 11 -19261 A | 1/1999 |
| JP | 11-029466 | 2/1999 |
| JP | A-11-180901 | 7/1999 |
| JP | 11-209642 | 8/1999 |
| JP | 2000-007570 | 1/2000 |
| JP | 2001-511135 | 7/2000 |
| JP | 2001-302517 | 10/2001 |
| JP | 2002-524535 | 6/2002 |
| JP | 2002-538113 | 11/2002 |
| JP | 2003-26607 A | 1/2003 |
| JP | A 03-026607 | 1/2003 |
| JP | 2003-201238 | 7/2003 |
| JP | 2005-053841 | 3/2005 |
| JP | 2005-518453 A | 6/2005 |
| JP | 2006-525270 | 11/2006 |
| JP | 2006-342108 | 12/2006 |
| JP | 2007-522076 | 8/2007 |
| JP | 2009-274988 | 12/2009 |
| JP | 2010-090151 | 4/2010 |
| JP | 2010-110185 | 5/2010 |
| KR | 1999-0036861 | 5/1999 |
| KR | 10-2006-0020616 A1 | 3/2006 |
| KR | 10-2010-0016396 | 2/2010 |
| RU | 2107496 | 3/1998 |
| RU | 2226096 | 3/2004 |
| RU | 2256446 | 7/2005 |
| RU | 2265434 | 12/2005 |
| WO | WO1992-15544 | 9/1992 |
| WO | 95/00130 A1 | 1/1995 |
| WO | WO1995-00130 | 1/1995 |
| WO | 98/14183 | 4/1998 |
| WO | 98/14183 A1 | 4/1998 |
| WO | WO 98/14183 | 4/1998 |
| WO | WO1998-14183 | 4/1998 |
| WO | WO 1998/032421 | 7/1998 |
| WO | WO 1999/015150 | 4/1999 |
| WO | WO 2000-015262 | 3/2000 |
| WO | 03/072734 A2 | 9/2003 |
| WO | 2004/005353 A1 | 1/2004 |
| WO | WO 2004/011423 | 2/2004 |
| WO | WO 2004/048323 | 6/2004 |
| WO | WO 2004/049095 A3 | 6/2004 |
| WO | WO 2005/004854 | 1/2005 |
| WO | 2005/028411 A1 | 3/2005 |
| WO | WO2005/028411 | 3/2005 |
| WO | WO 2005/028411 | 3/2005 |
| WO | 2005/120495 A1 | 12/2005 |
| WO | WO 2005/120495 A1 | 12/2005 |
| WO | WO 2006/039685 | 4/2006 |
| WO | 2006/093348 A2 | 9/2006 |
| WO | WO2006/093348 | 9/2006 |
| WO | 2006/104610 A2 | 10/2006 |
| WO | WO 2006/104610 | 10/2006 |
| WO | WO 2007/072529 | 6/2007 |
| WO | WO 2008/014685 | 2/2008 |
| WO | WO 2008/027687 | 3/2008 |
| WO | WO 2008/102563 | 8/2008 |
| WO | 2008/136900 A1 | 11/2008 |
| WO | WO 2008/135090 * | 11/2008 |
| WO | WO 2008/136900 | 11/2008 |
| WO | WO 2009/058399 | 5/2009 |
| WO | WO 2009/111688 | 9/2009 |
| WO | WO 2010/151314 | 12/2010 |
| WO | WO 2011/152869 | 12/2011 |
| WO | WO 2017/165667 | 9/2017 |

OTHER PUBLICATIONS

Ohga, Eijiro, et al., "The relationship between adhesion molecules and hypoxia," Nippon Rinsho, 2000, vol. 58, No. 8, pp. 1587-1591.
Singer, Mervyn, et al., "Intravenous crocetinate prolongs survival in a rat model of lethal hypoxemia," Crit Care Med, 2000, vol. 28, No. 6, pp. 1968-1972.
The Lung perspectives, 2001, vol. 9, No. 2, pp. 161-165.
Notice of Reasons for Rejection dated Nov. 24, 2015, issued in Japanese Patent Application No. P2015-011575, which corresponds to PCT/US2006/006422, and English translation.
Final Rejection dated Nov. 24, 2015, issued in Japanese Patent Application No. P2013-513151, which corresponds to PCT/US2011/000997, and English translation.
Notice of Preliminary Rejection dated Nov. 24, 2015, issued in Korean Application No. 10-2010-7010445, which corresponds to PCT/US2008/012440, and English translation.
3rd Notification of Office Action dated Dec. 14, 2015, issued in Chinese Application No. 201180033875.6, which corresponds to PCT/US2011/000997, and English translation.
Search Report dated Dec. 14, 2015, issued in Chinese Application No. 201180033875.6, which corresponds to PCT/US2011/000997, and English translation.
Brown, J. Martin, et al., "The Unique Physiology of Solid Tumors: Opportunities (and Problems) for Cancer Therapy," Cancer Research, vol. 58, 1998, pp. 1408-1416.
Maehara, Yoshihiko, Fukuoka Medical Journal, vol. 88, No. 11, 1997, pp. 337-344.
Feb. 25, 2015 Office Action from the Australian Patent Office for applicant's application corresponding to PCT Application No. PCT/US2011/000997.

(56) References Cited

OTHER PUBLICATIONS

Feb. 1, 2015 Office Action from the Israel Patent Office for applicant's application corresponding to PCT Application No. PCT/US2003/026424.
Office Action dated Mar. 16, 2016, issued in U.S. Appl. No. 13/507,365.
Final Rejection dated Mar. 1, 2016, issued in Japanese Patent Application No. P2014-061897, which corresponds to PCT/US2008/004708, and English translation.
Apr. 29, 2015 U.S. Office Action issued in U.S. Appl. No. 12/801,726.
May 5, 2015 Chinese Office Action for national phase of PCT/US2008/004708, and English translation.
Apr. 21, 2015 Japanese Office Action for national phase of PCT/US2011/000997 and English translation.
Design and Evaluation of Oral Formulation, Jiho, Inc., Feb. 10, 1995, pp. 337-339.
Pharmaceutical Formulation Strategies and New Technology, published by CMC Co. Ltd., Mar. 31, 2007, first printing, p. 88.
5th Notification of Office Action dated Jun. 21, 2016, issued in Chinese Patent Application No. 200880015671.8, which is the national phase of PCT/US2008/04708, and English translation.
Final Rejection dated Jun. 28, 2016, issued in Japanese Patent Application No. 2015-011575, which is the national phase of PCT/US06/06422, and English translation.
Communication Pursuant to Article 94(3) EPC dated Jul. 6, 2016, issued in European Patent Application No. 12 166 293.6, which is the national phase of PCT/US06/06422.
Lancrajan, Ioana, et al., "Carotenoid incorporation into natural membranes from artificial carriers: liposomes and β-cyclodextrins," Chemistry and Physics of Lipids, vol. 112, No. 1, 2001, pp. 1-10, XP55044152.
Pfitzner, Inka, et al., "Carotenoid: methyl-β-cyclodextrin formulations: an improved method for supplementation of cultured cells," Biochimica et Biophysica Acta, vol. 1474, No. 2, 2000, pp. 163-168, XP4276552.
Polyakov, Nikolai E., "Inclusion Complexes of Carotenoids with Cyclodextrins: $^1$H NMR, EPR, and Optical Studies," Free Radical Biology & Medicine, vol. 36, No. 7, 2004, pp. 872-880, XP27231510.
Rowinsky, Eric K., et al., "Novel Radiation Sensitizers Targeting Tissue Hypoxia," Oncology, vol. 13, No. 10, Supplement No. 5, Oct. 1999, pp. 61-70, XP009044613.
Wilkins, E. S., et al., "The Effect of Crocetin on the Irradiation of Walker-256: in Vitro and in Vivo Studies," Cancer Biochem. Biophys., vol. 3, 1979, pp. 71-74, XP008157982.
Chinese Office Action dated Jun. 24, 2015 for National Phase of PCT/US03/26424 (with translation).
Buchta et al., "Eine Totalsynthese des „all"-trans-Crocetin-dimethylesters[2]", Chemischte Berichte Jahrg. 93, 1960, pp. 1349-1353.
Jul. 21, 2015 India Office Action for National Phase of PCT/US2003/26424.
Jul. 23, 2015 India Office Action for National Phase of PCT/US2008/012440.
"Synergistic Effects of Chemical Enhancers and Therapeutic Ultrasound on Transdermal Drug Delivery", Mark E. Johnson et al., American Chemical Society and American Pharmaceutical Association, Journal of Pharmaceutical Sciences, vol. 85, No. 7, Jul. 1996, pp. 670-679.
Aug. 13, 2015 USPTO Office Action for U.S. Appl. No. 13/507,365.
5th Notification of Office Action dated Aug. 17, 2015, issued in Chinese Patent Application No. 200880114310.9 and English translation.
3rd Notification of Office Action dated Sep. 25, 2015, issued in Chinese Patent Application No. 201080027664.7 and English translation.
Search Report dated Sep. 15, 2015, issued in Chinese Patent Application No. 201080027664.7 and English translation.

Stennett, Amanda K., et al., "trans-Sodium Crocetinate and Diffusion Enhancement," J. Phys. Chem. B, vol. 110, Issue 37, 2006, pp. 18078-18080.
Communication pursuant to Article 94(3) EPC dated May 17, 2016, issued in European Patent Application No. 03 711 221.6, which is the national phase of PCT/US03/05521.
Communication pursuant to Article 94(3) EPC dated May 19, 2016, issued in European Patent Application No. 03 818 748.0, which is the national phase of PCT/US03/26424.
Communication pursuant to Article 94(3) EPC dated Jun. 3, 2016, issued in European Patent Application No. 11 790 107.4, which is the national phase of PCT/US2011/000997.
Notice of Reasons for Rejection dated Jun. 21, 2016, issued in Japanese Patent Application No. 2015-159872 and English translation.
Koynova, R., et al., "Modulation of lipid phase behavior by kosmotropic and chaotropic solutes—Experiment and thermodynamic theory," Eur Biophys J, vol. 25, 1997, pp. 261-274.
Magazù, Salvatore, et al., "α,α-Trehalose-Water Solutions. VIII. Study of the Diffusive Dynamics of Water by High-Resolution Quasi Elastic Neutron Scattering," J. Phys. Chem. B, vol. 110, No. 2, 2006, pp. 1020-1025.
Jun. 4, 2015 U.S. Office Action for U.S. Appl. No. 13/621,650.
Korean Office Action dated May 27, 2015 for Application No. 10-2009-7023432 (national phase of PCT/US2008/04708) (with translation).
Nov. 12, 2015 USPTO Office Action for U.S. Appl. No. 12/801,726.
Apr. 14, 2015 Japanese Office Action for national phase of PCT/US2008/012440, and English translation.
Apr. 21, 2015 Japanese Office Action for national phase of PCT/US2008/04708, and English translation.
Notice of Preliminary Rejection dated Jul. 26, 2016, issued in South Korean Patent Application No. 10-2012-7001265, which is the national phase of PCT/US2010/001794, and English translation.
Office Action dated Aug. 3, 2016, issued in Canadian Patent Application No. 2,703,946, which corresponds to PCT/US2008/012440.
Japanese Official Action dated Sep. 8, 2015.
Sep. 30, 2015 USPTO Office Action for U.S. Appl. No. 13/137,337.
Wirz et al, Helv. Chim. ACTA, vol. 43, No. 6, 1960, pp. 1738-1745.
Osler et al, Helv. Chim. ACTA, vol. 40, No. 5, 1957, pp. 1242-1249.
Wenkert et al, J. Org. Chem, vol. 55, No. 25, 1990, pp. 6203-6214.
Gibson et al, J. Org. Chem., vol. 41, No. 5, 1976, pp. 791-792.
EPO office action dated Oct. 27, 2015 that issued in the European application that corresponds to PCT//US03/05521.
Jul. 9, 2015 USPTO Office Action for one of applicant's U.S. Appl. No. 13/137,324.
Search Report dated Oct. 21, 2016, issued in Chinese Application No. 201510128602.X, which is a national phase of PCT/US06/06422, and English translation.
First Notification of Office Action dated Oct. 31, 2016, issued in Chinese Application No. 201510128602.X, which is a national phase of PCT/US06/06422, and English translation.
Decision of Rejection dated Nov. 10, 2016, issued in Chinese Application No. 201080027664.7, which is a national phase of PCT/US2010/001794, and English translation.
Office Action dated Nov. 14, 2016, issued in U.S. Appl. No. 12/801,726, which corresponds to PCT/US2010/001794.
Magesh, V., et al., "Studies on the anti-tumor effect of crocetin against benzo (a)pyrene induced lung cancer in Swiss albino mice," Biomedicine, 3rd and 4th Edition, vol. 23, Dec. 31, 2003, pp. 96-99.
Office Action dated Aug. 23, 2016, issued in Indian Patent Application No. 6834/delnp/2009, which is the national phase of PCT/US2008/04708.
Office Action dated Aug. 31, 2016, issued in Canadian Patent Application No. 2,598,882, which is the national phase of PCT/US2006/06422.
Tyssandier et al., "Processing of vegetable-borne carotenoids in the human stomach and duodenum," Am J Physiol Gastrointest Liver Physiol, 2003, 284: G913-G923.
Examination Report No. 1 dated Dec. 1, 2016, issued in Australian Patent Application No. 2016201192, which is a National phase of PCT/US2011/000997.

(56) References Cited

OTHER PUBLICATIONS

U.S. Appl. No. 60/907,718, filed Apr. 13, 2007, Gainer.
U.S. Appl. No. 61/001,095, filed Oct. 31, 2007, Gainer.
U.S. Appl. No. 61/350,804, filed Jun. 2, 2010, Gainer et al.
Abstract of JP 11-209642 (Aug. 3, 1999).
Abstract of JP-2001-302517 (Oct. 31, 2001).
Abstract of JP-A 03-026607 (Jan. 29, 2003).
Abusuev, A.A., Clinical Course of Myocardial Infarction in Treatment with Perfluorane, in Perfluorocarbon Compounds in Experimental and Clinical Medicine, Collected Works of the Russian Scientific Conference, St. Petersburg, 2004, p. 12 (No English translation available.).
Ahmad, A.S. et al., "Neuroprotection by crocetin in a hemiparkinsonian rat model," Pharmacology Biochemistry and Behavior, 2005, vol. 81, pp. 805-813.
Bennett, M.H. et al., "Hyperbaric oxygen therapy for late radiation tissue injury (Review)," 2005, The Cochrane Collaboration Published by John Wiley & Sons, Ltd., Issue 2.
Borisova, I.V. et al., "Renal and Neuroprotective Effects of Perfluorane in Induced Toxic Renal Injury in Rats," Medline.ru-Biomeditsinskii Zhurnal, 2004, vol. 5, Art. 16, pp. 136-139.
Britton, G. et al., "Isolation and Analysis," 1995, Carotenoids, vol. IA, pp. 103-107; p. 283, Birkhauser Verlag, Basel.
Broderick, J.P., et al., "Finding the Most Powerful Measures of the Effectiveness of Tissue Plasminogen Activator in the NINDS tPA Stroke Trial," 2000, Stroke, vol. 31, No. 10, pp. 2335-2341.
Buchta, E. et al., "The Total Synthesis of trans-2,2-Bisdimethyl-crocetin-dimetyl ester and trans-Crocetin-dimethyl ester," 1959, Naturwiss (No English translation available.).
Bui, Q-C et al., "The Efficacy of Hyperbaric Oxygen Therapy in the Treatment of Radiation-Induced Late Side Effects," 2004, Int. J. Radiation Oncology Biol. Phys., vol. 60, No. 3, pp. 871-878.
Burukhina, A.N. et al., "Experience of Using Perfluorane in Treating Acute Massive Hemorrhage in Obstetric Practice, in Collected Works of the 12th Scientific and Practical Conference of Physicians Topical Issues in Modern Medicine," 2002, Novosibirsk, Chapter 2, pp. 39-40.
Calvo, W. et al., "Time—and dose-related changes in the white matter of the rat brain after single doses of X rays," 1988, The British Journal of Radiology, vol. 61, pp. 1043-1052.
Cheng, N.T. et al., "Intravenous thrombolysis for acute ischemic stroke within 3 hours versus between 3 and 4.5 hours of symptom onset," 2015, The Neurohospitalist, vol. 5, Issue 3, pp. 101-109.
Cianci, P. "Hyperbaric therapy for radiation injury," 1999, Radiation Injury, Advances in Management and Prevention edited by J.L. Meyer, et al., pp. 98-109.
Clark, W.M., et al., "The rtPA (Alteplase) 0- to 6-Hour Acute Stroke Trial, Part A (A0276g): Results of a Double-Blind, Placebo-Controlled, Multicenter Study," 2000, Stroke, vol. 31, No. 4, pp. 311-816.
Coppola, G.M., "Amberlyst-15, A Superior Acid Catalyst for the Cleavage of Actetals," Dec. 1984, Syn. Communications 1021.
Cutright, D.E. et al., "Long-Term Effects of Radiation on the Vascularity of Rat Bone—Quantitative Measurements with a New Technique," 1971, Radiation Research, vol. 48, pp. 402-408.
Database Caplus, Chemical Abstracts Service, Columbus, Ohio, US, 1988, XP002317165 [JP 63 059831].
Database Caplus, Chemical Abstracts Service, Columbus, Ohio, US, 1993, XP002317166 [JP 05 032531].
Denninghoff et al., "Retinal Imaging Techniques in Diabetes," 2000, Diabetes Technology & Therapeutics, vol. 2, No. 1, pp. 111-113.
Finney, J., et al., "Protection of the ischemic heart with DMSO alone or DMSO with hydrogen peroxide," Mar. 15, 1967, Annals of the New York Academy of Sciences, vol. 141, No. I, pp. 231-241.
Gainer, J.L., et al., "Oxygen diffusion and atherosclerosis," 1974, Atherosclerosis, vol. 19, pp. 135-138.
Gainer, J.L. et al., "Using Excess Volume of Mixing to Correlate Diffusivities in Liquids," 1982, Chem. Eng. Commun., vol. 15, pp. 323-329.
Gainer, J.L., et al., "The Effect of Crocetin on Hemorrhagic Shock in Rats," 1993, Circulatory Shock, vol. 41, pp. 1-7.
Gainer, J.L., "Altering Diffusivities in Dilute Polymeric and Biological Solutions," 1994, Ind. Engr. Chem. Research, vol. 33, pp. 2341-2344.
Gainer, J.L. et al., "The effect of trans sodium crocetinate (TSC) in a rat oleic acid model of acute lung injury," 2005, Pulmonary Pharmacology & Therapeutics, Academic Press, GB, vol. 18, No. 3, pp. 213-216, XP004737366.
Gainer, John L., "Trans-Sodium Crocetinate for Treating Hypoxia/Ischemic," 2008, Expert Opinion on Investigational Drugs, vol. 17, No. 6, pp. 917-924.
General Information on Perfluorane, Medline.ru-Biomeditsinskii Zhumal, 2004, vol. 5, Art. 16, pp. 68-69, www.medline.ru/public/art/tom5/art8-perf2.phtm (with English translation).
Ghandehari, K. et al., "Thrombolysis in stroke patients; Problems and limitations," 2010, Iran Journal of Med. Sci., vol. 35, Issue 2, pp. 145-148.
Giassi, L.J. et al., "Trans Sodium Crocetinate Restores Blood Pressure, Heart Rate, and Plasma Lactate after Hemorrhagic Shock," 2001, Journal of Trauma, vol. 51, pp. 932-938.
Giassi, L.J., et al., "Trans Sodium Crocetinate for Hemorrhagic Shock: Effect of Time Delay in Initiating Therapy," 2002, Shock, vol. 18, No. 6, pp. 585-588.
Gill, A.L. et al., "Hyperbaric oxygen: its uses, mechanisms of action and outcomes," 2004, Q J Med, vol. 97, pp. 385-395.
Goldstick, T.K., Ph.D, "Diffusion of Oxygen in Protein Solutions," 1966, Dissertation, University of California, Berkeley, CA, pp. 13-28.
Gree, R. et al., "Fumaraldehyde Monodimethyl Acetal: An Easily Accessible and Versatile Intermediate", 1986, Tetrahedron Letters, vol. 27, No. 41, pp. 4983-4986.
Greenwood, T.W. et al., "Hyperbaric Oxygen and Wound Healing in Post-Irradiation Head and Neck Surgery," May 1973, Brit. J. Surg., vol. 60, No. 5, pp. 394-397.
Group, N.r.-P.S.S., "Tissue Plasminogen Activator for Acute Ischemic Stroke," 1995, The New England Journal of Medicine, vol. 333, No. 24, pp. 1581-1587.
Holland, R.A.B. et al., "Kinetics of O2 Uptake and Release by Red Cells in Stopped-Flow Apparatus: Effects of unstirred Layer," 1985, Respiration Physiology, vol. 59, pp. 71-91.
Holloway, G.M., et al., "The carotenoid crocetin enhances pulmonary oxygenation," The American Physiological Society, 1988, pp. 683-686, Department of Chemical Engineering, and Dept. of Anesthesiology, School of Medicine, Univ. of VA, Charlotteville, Va.
Huxley, V.H., et al., "The Effect of the Red Cell Membrane and a Diffusion Boundary Layer on the Rate of Oxygen Uptake by Human Erythrocytes," 1981, J. Physiol., vol. 316, pp. 75-83.
Ingall, T., "Stroke-Incidence, Mortality, Morbidity and Risk," 2004, Journal of Insurance Medicine, vol. 36, No. 2, pp. 143-152.
International Preliminary Report on Patentability dated May 25, 2007 in PCT/US2003/026424.
International Preliminary Report on Patentability dated Jan. 12, 2012 in PCT/US2010/001794.
International Search Report and Written Opinion for International Application No. PCT/US2010/001794 dated Sep. 1, 2010.
International Preliminary Report on Patentability (IPRP) (Chapter I) for PCT/US2011/000997, dated Dec. 13, 2012.
International Search Report for International Application No. PCT/US2003/005521 dated Dec. 24, 2003.
International Preliminary Report on Patentability for International Application No. PCT/US2003/005521 prepared Aug. 23, 2004.
International Search Report for International Application No. PCT/US2003/026424 dated Nov. 5, 2004.
International Preliminary Report on Patentability for International Application No. PCT/US2003/026424 prepared May 10, 2007.
International Search Report for International Application No. PCT/US2006/006422 dated Oct. 19, 2006.
International Preliminary Report on Patentability for International Application No. PCT/US2006/006422 dated Aug. 28, 2007.
International Search Report and Written Opinion for International Application No. PCT/US2008/004708 dated Jul. 22, 2008.

(56) References Cited

OTHER PUBLICATIONS

International Preliminary Report on Patentability for International Application No. PCT/US2008/004708 dated Oct. 13, 2009.
International Search Report and Written Opinion for International Application No. PCT/US2008/012440 dated Mar. 25, 2009.
International Preliminary Report on Patentability for International Application No. PCT/US2008/012440 dated May 4, 2010.
International Search Report and Written Opinion for International Application No. PCT/US2011/000997 dated Sep. 9, 2011.
International Preliminary Report on Patentability for International Application No. PCT/US2011/000997 dated Dec. 4, 2012.
Invitation to Pay Additional Fees and, Where Applicable, Protest Fee dated Jan. 13, 2009 in PCT/US2008/012440.
Jansen, F.J.H.M., et al., "Synthesis and Characterization of All-E $(12,12'-{}^{13}C_2)$-, $(13,13'-{}^{13}C_2)$-, $(14,14'-{}^{13}C_2)$-, $(15,15'-{}^{13}C_2)$- and $(20,20'-{}^{13}C_2)$astaxanthin," 1994, Recl. Trav. Chem. Pays-Bas, vol. 113, p. 552.
Kalani, M., et al., "Hyperbaric Oxygen (HBO) Therapy in Treatment of Diabetic Foot Ulcers Long-term Follow-up," 2002, Journal of Diabetes & Its Complications, vol. 16, No. 2, pp. 153-158.
Kamiryo, T. et al., "Histological Changes in the Normal Rat Brain After Gamma Irradiation," 1996, Acta Neurochir (Wien), 138, pp. 451-459.
Kamiryo, T. et al., "Radiosurgery-induced Microvascular Alterations Precede Necrosis of the Brain Neuropil," Aug. 2001, Neurosurgery, vol. 49, No. 2, pp. 409-415.
Kichev, G.S. et al., "Experience of Using Perfluorane in Treating Critical Conditions of Various Geneses," 2004, Medline.ru-Biomeditsinskii Zhurnal, vol. 5, Art. 53, pp. 175-177.
Laidig, K.E. et al., "Altering Diffusivity in Biological Solutions through Modification of Solution Structure and Dynamics," 1998, Journal of the American Chemical Society, vol. 120, No. 36, pp. 9394-9395, XP002970835.
Lang, et al., "Parkinson's Disease," 1998, New England Journal of Medicine, vol. 339, No. 15, pp. 1044-1053.
Lapchak, P.A., et al., "Neuroprotective Effects of the Spin Trap Agent Disodium-[(tert-buty/imino)methyl]benzene-1,3-disulfonate N-Oxide (Generic NXY-059) in a Rabbit Small Clot Embolic Stroke Model: Combination Studies With the Thrombolytic Tissue Plasminogen Activator," 2002, Stroke, vol. 33, No. 5, pp. 1411-1415.
Lapchak, P.A., et al., "Comparison of Tenecteplase With Alteplase on Clinical Rating Scores Following Small Clot Embolic Strokes in Rabbits," 2004, Experimental Neurology, vol. 185, No. 1, pp. 154-159.
Lapchak, P.A. et al., "Transcranial Infrared laser Therapy Improves Clinical Rating Scores After Embolic Strokes in Rabbits," 2004, Stroke, vol. 35, No. 8, pp. 1985-1988.
Lapchak, P.A., "Memantime, an uncompetitive low affinity NMDA open-channel antagonist improves clinical rating scores in a multiple infarct embolic stroke model in rabbits," 2006, Brain Research, vol. 1088, No. 1 , pp. 141-147.
Lapchak, P.A., et al., "Advances in Ischemic Stroke Treatment: Neuroprotective and Combination Therapies," 2007, Expert Opin. Emerging Drugs, vol. 12, No. 2, pp. 1-16.
Lapchak, P.A., "The Phenylpropanoid Micronutrient Chlorogenic Acid Improves Clinical Rating Scores in Rabbits Following Multiple Infarct Ischemic Strokes: Synergism With Tissue Plasminogen Activator," 2007, Experimental Neurology, vol. 205, No. 2, pp. 407-413.
Lapchak, P.A., et al., "Transcranial Near-Infrared Light Therapy Improves Motor Function Following Embolic Strokes in Rabbits: An Extended Therapeutic Window Study Using Continuous and Pulse Frequency Delivery Modes," 2007, Neuroscience, vol. 148, p. 907-914.
Lapchak, P.A., et al., "Therapeutic Window for Nonerythropoietic carbamylated-erythropoietin to Improve Motor Function Following Multiple Infarct Ischemic Strokes in New Zealand White Rabbits," 2008, Brain Research, vol. 1238, pp. 208-214.
Lapchak, P.A., "Efficacy and safety profile of the carotenoid trans sodium crocetinate administered to rabbits following multiple infarct ischemic strokes: A combination therapy study with tissue plasminogen activator," Jan. 14, 2010, Brain Research, vol. 1309, pp. 136-145, XP-002686117.
Letham, D.S., et al., "The Synthesis of Radioisotopically Labelled Zeatin," 1971, Phytochemistry, vol. 10, pp. 2077.
Lide, D.R. Ph.D., "CRC Handbook of Chemistry and Physics," 1998, CRC Press, Boca Raton, FL, pp. 6-181.
Lishner, M. et al., "Treatment of Diabetic Perforating Ulcers (Mal Perforant) with Local Dimethylsulfoxide," 1985, J. Am. Geriatr. Soc., vol. 33, pp. 41-43.
Lyubimova, N. et al., "Experimental evidence to support the hypothesis that damage to vascular endothelium plays the primary role in the development of late radiation-induced CNS injury," 2004, The British Journal of Radiology, vol. 77, pp. 488-492.
Marx, R.E., D.D.S., "Osteoradionecrosis: A New Concept of its Pathophysiology," 1983, J. Oral Maxillofac. Surg, vol. 41, pp. 283-288.
Marx, R.E., D.D.S., et al., "Relationship of Oxygen Dose to Angiogenesis Induction in Irradiated Tissue," Nov. 1990, The American Journal of Surgery, vol. 160, pp. 519-524.
Mayer, R. et al., "Hyperbaric Oxygen and Radiotherapy," 2005, Strahlenther Onkol, No. 2, pp. 113-123.
Miyagawa, H. et al., "Pathogenesis of delayed radiation injury in the rat spinal cord after X-ray irradiation," 1996, Neuropathology, vol. 16, pp. 126-132.
Moelbert, S. et al., "Kosmotropes and chaotropes: modeling preferential exclusion, binding and aggregate stability," 2004, Biophysical Chemistry, vol. 112, pp. 45-57.
Notification Concerning Transmittal of International Preliminary Report on Patentability (Chapter 1 of the Patent Cooperation Treaty) for International Application No. PCT/US2008/012440 dated May 14, 2010.
Okeda, R., "Pathological changes in the cerebral medullary arteries of five autopsy cases of malignant nephrosclerosis: Observation by morphometry and reconstruction of serial sections," 2003, Neuropathology, vol. 23, pp. 153-160.
Okonkwo, D.O., et al., "Trans-sodium crocetinate increases oxygen delivery to brain parenchyma in rats on oxygen supplementation," 2003, Neuroscience Letters, vol. 352, pp. 97-100.
Pauling, L., "Recent Work on the Configuration and Electronic Structure of Molecules; with some Applications to Natural Products," 1939, Fortschr. Chem. Org. Naturst., vol. 3, No. 303, pp. 203-235.
Pfander, H. et al., "Carotenoid synthesis: A progress report," 1997, Pure & Appl. Chem., vol. 69, No. 10, pp. 2047-2060.
Pharmacia, 1991, vol. 27, No. 7, pp. 703-705.
RN: 120523-11-7; CN: 2,4,6,8,10, 12,14,16,18-Eicosanonaenedioic acid, 4,8, 13,17-tetramethyl-potassium sodium salt, 1989.
RN: 147484-59-1; CN: 2,4,6,8-Decatetraenedioic acid, disodium salt, 1993.
RN: 33261-80-2; CN: 2,4,6,8,10,12,14,16,18-Eicosanonaenedioic acid, 4,8,13,17-tetramethyl-dipotassium salt, 1984.
RN: 33261-81-3; CN: 2,4,6,8,10,12,14,16,18-Eicosanonaenedioic acid, 4,8,13,17-tetramethyl-disodium salt, 1984.
Roy, J.W., et al, "A Novel Fluid Resuscitation Therapy for Hemorrhagic Shock," 1998, Shock, vol. 10, No. 3, pp. 213-217.
Schwieter, U., et al., "Synthesen in der Carotinoid-Reiche 20. Mitteilung Neu Synthesen von Apocarotinoiden," 1966, Helvetica Chimica Acta, vol. 1, pp. 369-390, XP-002575142. No English Translation Available.
Secor, R.M., "The Effect of Concentration on Diffusion Coefficient in Polymer Solutions," 1965, A.I.Ch.E. Journal, vol. 11, No. 3, pp. 452-456.
Seyde, W.C., et al., "Carotenoid Compound Crocetin Improves Cerebral Oxygenation in Hemorrhaged Rats," 1986, Journal of Cerebral Blood Flow and Metabolism, vol. 6, No. 6, pp. 703-707.
Shi, Nihon Butsuri Gakkai, "Structure and Function of Cartenoid in Photosynthetic System," 1995, Journal of the Physical Society of Japan, vol. 50, No. 7, pp. 555-561.

(56) References Cited

OTHER PUBLICATIONS

Snyder, J.M., et al., "cis-trans Isomerization of Unsaturated Fatty Acids with p-Toluenesulfinic Acid," 1982, J. Am. Oil Chem. Soc., vol. 59, pp. 469-470.
Streitwieser et al., Introduction to Organic Chemistry, 2nd Ed., 1981, pp. 504-505.
Supplementary Partial European Search Report in Feb. 25, 2005 based on Application No. EP 03 71 1221.
Supplementary Partial European Search Report in Apr. 21, 2005 based on Application No. EP 03 71 1221.
Supplementary Partial European Search Report dated Nov. 7, 2006.
Supplementary European Search Report dated Apr. 29, 2010 issued by the European Patent Office in one of Applicants' corresponding foreign applications.
Supplementary European Search Report dated Dec. 8, 2010 (corresponding to applicant's European Regional Phase Patent Application No. EP 08844993.9 based on International Patent Application No. PCT/US2008/012440 filed on Oct. 31, 2008).
Supplementary European Search Report dated Oct. 29, 2012 issued by the European Patent Office and Preliminary Opinion.
Supplementary Extended European Search Report dated Nov. 21, 2012 issued by the European Patent Office and Preliminary Opinion.
Supplementary (Extended) European Search Report dated Oct. 21, 2013 in European Patent Application No. EP 11790107.4 issued from PCT/US2011/000997 filed on Jun. 2, 2011, together with the Written Opinion.
Supplementary Extended European Search Report dated Mar. 28, 2013 issued by the European Patent Office and Written Opinion.
Tong, Linhui, "Cyclodextrins Chemistry: Fundamentals and Application," Mar. 2001, Science Press, p. 360-364.
Wang, Y. et al., "The Effect of Trans-Sodium Crocetinate in a Model of Intracranial Hemorrhage," Nov. 15, 2008, Abstracts of the Annual Meeting of the Society for Neuroscience, Society for Neuroscience Abstract Viewer and Itinerary Planner, vol. 38, 2 pp., Washington, DC, XP009163975.
White, D.C., M.D., "The Histopathologic basis for functional decrements in late radiation injury in diverse organs," 1976, Cancer, vol. 37, pp. 1126-1143, February Supplement.
Widmer, E. et al., "Technical Procedures for the Syntheses of Carotenoids and Related Compounds," 1990, Helvetica Chemica Acta, vol. 73, pp. 861-867.
Williamson et al., "An experimental study of the use of hyperbaric oxygen to reduce the side effects of radiation treatment for malignant disease," 2007, Int. J. Oral Maxillofac. Surg., vol. 36, pp. 533-540.
Written Opinion for International Application No. PCT/US2006/006422 dated Oct. 19, 2006.
Wurtman, R.J., "Alzheimer's Disease," 1985, Scientific American, vol. 252.
Yamaguchi, K. et al., "Kinetics of O2 uptake and release by human erythrocytes studied by a stopped-flow technique," 1985, The American Physiological Society, vol. 58, pp. 1215-1224.
Zheng, S. et al., "Crocetin Attenuates Atherosclerosis in Hyperlipidemic Rabbits Through Inhibition of LDL Oxidation," Jan. 2006, J. Cardiovasc. Pharrnacol, vol. 47, No. 1, pp. 70-76, XP009135396, ISSN: 0160-2446.
Australian Office Action dated Jun. 25, 2008 from corresponding Australian Patent Office.
Australian Office Action dated Mar. 26, 2010 in Applicant's Australian Application No. 2003265617.
Australian Office Action dated Oct. 25, 2010 issued by the Australian Patent Office in one of Applicants' corresponding foreign applications.
Australian Office Action dated Dec. 23, 2011.
Australian Office Action dated Dec. 3, 2014 from the Australian Patent Office for applicant's Australian application corresponding to PCT Application No. PCT/US03/26424.
Australian Office Action dated Dec. 10, 2014 from applicant's Australian application corresponding to PCT Application No. PCT/US2008/012440.
Canadian Office Action dated Mar. 26, 2013, for applicant's Canadian Patent Application No. 2,598,882 corresponding to PCT/US06/006422 filed Feb. 24, 2006.
Canadian Office Action dated May 30, 2013, for applicant's Canadian Patent Application No. 2,683,760 corresponding to PCT/US2008/004708 filed Apr. 11, 2008.
Canadian Office Action dated Oct. 20, 2009 from Canadian Application No. 2,477,245.
Canadian Office Action dated Jul. 7, 2010 in corresponding Canadian Application No. 2,477,245.
Canadian Office Action dated Oct. 26, 2010 in corresponding Canadian Application No. 2,537,210.
Canadian Office Action dated Jul. 5, 2011 in corresponding Canadian Application No. 2,537,210.
Canadian Office Action dated Nov. 4, 2014 in Canadian Patent Application No. 2,703,946 from national phase of PCT/US2008/012440.
Chinese Office Action dated Nov. 7, 2008 in a corresponding application owned by the applicants in Chinese Application No. 03826969.4.
Chinese Third Office Action in Chinese Patent Application No. 03804566.4 dated Jan. 23, 2009 (English Translation Only).
Chinese Office Action and its English Translation dated Feb. 12, 2010 in the Assignee's Chinese application relating to PCT/US2006/006422.
Chinese Office Action dated Mar. 29, 2010 from Chinese Patent Application No. 03826969.4 based on PCT/US2003/026424.
Chinese Office Action and its English Translation dated Feb. 21, 2011 in Assignee's Chinese Patent Application No. 200680013663.0 based on PCT/US2006/006422.
Chinese Office Action and its English Translation dated Apr. 6, 2011 from Chinese Patent Application No. 200680013663.0 based on PCT/US2006/006422.
Chinese Office Action dated Jun. 30, 2011 in Chinese Application No. 2008801143109 (English Translation Only).
Chinese Office Action and its English Translation dated Jan. 18, 2012 in Chinese Patent Application No. 200680013663.0 based on PCT/US2006/006422.
Chinese Office Action and its English translation dated May 3, 2012, from Chinese Patent Application No. 03804566.4 based on PCT/US2003/005521.
Chinese Office Action and its English translation dated Jun. 6, 2012, from Chinese Patent Application No. 200880015671.8 based on PCT/US2008/004708.
Chinese Office Action and its English Translation dated Jun. 14, 2012 from Chinese Patent Application No. 200880114310.9 that corresponds to PCT/US2008/012440.
Chinese Office Action and its English Translation dated Jan. 28, 2013, from Chinese Patent Application No. 200880015671.8 that corresponds to PCT/US2008/004708.
Chinese Patent Office Decision of Rejection dated May 2, 2013 and its English translation, corresponding to PCT/US2006/06422 filed on Feb. 24, 2006.
Chinese Office Action dated May 6, 2013, from Chinese Patent Application No. 201080027664.7 that corresponds to PCT/US2010/001794, and its English translation.
Chinese Office Action dated Jul. 9, 2013, from Chinese Patent Application No. 200880114310.9 that corresponds to IPCT/US2008/012440, and its English translation.
Chinese Office Action and its English translation dated Nov. 1, 2013, from Chinese Patent Application No. 201180033875.6 that corresponds to PCT/US2011/000997.
Chinese Office Action and its English translation dated Mar. 19, 2014, from Chinese Patent Application No. 200880015671.8 that corresponds to PCT/US2008/004708.
Chinese Office Action and its English translation dated Mar. 31, 2014, from Chinese Patent Application No. 201210063676.6 that corresponds to PCT/US2003/026424, filed Aug. 25, 2003.
Chinese Office Action and English Translation dated Jul. 21, 2014 issued in Chinese Patent Application No. 200680013663.0, 9 pp.
Chinese Office Action and English Translation dated Jul. 24, 2014 issued in Chinese Patent Application No. 200880114310.9, 19 pp.

(56) References Cited

OTHER PUBLICATIONS

Chinese Office Action dated Aug. 15, 2014 issued in Chinese Patent Application No. 201080027664.7 and English Translation, 13 pp.
Chinese Office Action and English Translation dated Dec. 8, 2014 (Reexamination Decision) from the Chinese Patent Office in applicant's Chinese Application corresponding to PCT Application No. PCT/US06/06422.
Chinese Notice and Office Action and English Translations dated Dec. 22, 2014 from the China Patent Office for applicant's China application corresponding to PCT Application No. PCT/US2011/000997.
Chinese Search Report dated Mar. 18, 2013, and its English translation.
Chinese Search Report dated Jun. 27, 2013, and its English translation.
Chinese Search Report and its English translation dated Mar. 19, 2014, from Chinese Patent Application No. 201210063676.6 that corresponds to PCT/US2003/026424, filed Aug. 25, 2003.
Eurasian Patent Office Action and its English translation dated Nov. 9, 2011.
Eurasian Patent Office Action and its English translation dated Nov. 17, 2011.
European Office Action dated Nov. 9, 2009 in Applicant's European application corresponding to PCT/US2003/005521.
European Office Action dated Nov. 9, 2009 in Applicant's European application corresponding to PCT/US2003/026424.
European Office Action dated Apr. 7, 2011, from European Patent Application No. EP 08742781.1.
European Office Action dated Oct. 17, 2011 from European Patent Application No. EP 08742781.1.
European Office Action dated Oct. 31, 2011, from European Patent Application No. EP 06758166.0.
European Office Action dated Apr. 25, 2012.
European Office Action dated Jun. 11, 2012, from European Patent Application No. EP 08742781.1.
European Office Action dated Mar. 12, 2014, from applicant's European Patent Application No. EP 12166293.6, corresponding to PCT/US2006/006422 filed Feb. 24, 2006.
European Office Action dated Nov. 21, 2014 from the EPO for applicant's EP Application No. 03818748.0 based on PCT/US2003/26424.
European Office Action dated Feb. 2, 2015 from the for applicant's application corresponding to PCT Application No. PCT/US2008/012440.
European Office Action dated Feb. 2, 2015 from the for applicant's application corresponding to PCT Application No. PCT/US03/05521.
Hungarian Novelty Search Report dated Nov. 5, 2009 (w/translation).
India Office Action dated Oct. 23, 2008 in a corresponding application owned by the applicants (India Patent App No. 676/DELNP/2006).
India Examination Report dated Apr. 12, 2010 issued by the India Patent Office in one of Applicants' corresponding foreign applications.
India Office Action (Examination Report) dated Feb. 21, 2013, for applicant's India Patent Application No. 6688/DELNP/2007 corresponding to PCT/US2006/006422 filed Feb. 24, 2006.
India Office Action dated Dec. 31, 2014 from the India Patent Office for applicant's India application corresponding to PCT Application No. PCT/US2008/04708.
Israeli Office Action dated Apr. 10, 2013, from applicant's Israel Patent Application No. 185460 corresponding to PCT/US06/06422 filed Feb. 24, 2006, and its English translation.
Israeli Office Action dated Oct. 29, 2013, from Israel Patent Application No. 201438 that corresponds to PCT/US2008/004708, and its English translation.
Israeli Office Action and English Translation dated May 4, 2014 from applicant's Israel Patent Application No. 185460 corresponding to PCT/US06/06422 filed Feb. 24, 2006.

Japanese Patent Office Action dated Jun. 2, 2009 and its English translation, cited in one of Assignee's Japanese Patent Application No. 2003-571422.
Japanese Patent Office Action dated Jun. 9, 2009 and its English translation, cited in one of Assignee's Japanese Patent Application No. 2005-509104.
Japanese Decision of Rejection dated Jan. 12, 2010 and its English translation, corresponding to PCT/US2003/005521, corresponding to Diffusion's U.S. Pat. No. 7,351,844.
Japanese Office Action and its English Translation dated Jan. 12, 2010 in the Assignee's Japanese application relating to PCT/US2003/026424.
Japanese Office Action and its English Translation dated Apr. 6, 2010 in the Assignee's Japanese application relating to PCT/US2006/006422.
Japanese Notice of Reasons for Rejection and its English Translation dated May 24, 2011 issued in Japanese Patent Appln. No. 2007-557157 (corresponding to PCT/US2006/006422).
Japanese Office Action and its English Translation dated Oct. 4, 2011.
Japanese Office Action and its English Translation dated Jul. 10, 2012 for Applicant's Japanese Patent Application No. 2009-274988 corresponding to PCT/US2003/005521, filed Feb. 25, 2003.
Japanese Office Action and its English Translation dated Jul. 10, 2012 from Japanese Application No. 2009-279890 based on PCT/US2003/026424.
Japanese Office Action (Notice of Reasons for Rejection) dated Jan. 29, 2013, for applicant's Japanese Patent Application No. 2010-503069 corresponding to PCT/US08/004708 filed Apr. 11, 2008, and its English translation.
Japanese Patent Office Action dated Feb. 19, 2013, from applicant's Japanese Patent Application No. 2009-279890, corresponding to PCT/US03/26424 filed Aug. 25, 2003, and its English translation.
Japanese Decision of Rejection dated May 21, 2013, from applicant's Japanese Patent Application No. 2010-110185 corresponding to PCT/US2003/05521 filed Feb. 25, 2003, and its English translation.
Japanese Office Action (Notice of Reasons for Rejection) and its English translation dated Jun. 4, 2013, from applicant's Japanese Patent Application No. 2011-209754 corresponding to PCT/US06/06422 filed Feb. 24, 2006.
Japanese Office Action (Reasons for Rejection) dated Jun. 18, 2013, in Japanese App. No. 2010-531078 (no English translation).
Japanese Office Action (Final Rejection) and its English translation dated Sep. 10, 2013, from applicant's Japanese Application No. P2009-279890 corresponding to PCT/US03/26424 filed Aug. 25, 2003.
Japanese Office Action (Final Rejection) and its English translation dated Nov. 26, 2013, from applicant's Japanese Application No. P2010-503069 corresponding to PCT/US08/004708 filed Apr. 11, 2008.
Japanese Office Action (Final Rejection) and its English translation dated Feb. 4, 2014 from applicant's Japanese Application No. P2011-209754 corresponding to PCT/US06/06422 filed Feb. 24, 2006.
Japanese Office Action and its English translation dated Apr. 22, 2014 from applicant's Japanese Application No. P2010-531078 corresponding to PCT/US08/012440 filed Oct. 31, 2008.
Japanese Office Action dated Jun. 24, 2014 issued in Japanese Patent Application No. P2012-516071 and English Translation, 10 pp.
Japanese Office Action and its English translation dated Sep. 9, 2014 issued in Japanese Patent Application No. P2010-531078, 6 pp.
Japanese Office Action and English Translation dated Sep. 9, 2014 issued in Japanese Patent Application No. 2013-197629, 6 pp.
Japanese Office Action and English translation dated Sep. 24, 2014 issued in Japanese Patent Application No. P2011-209754, 5 pp.
Japanese Office Action dated Jan. 27, 2015 from the for applicant's application corresponding to PCT Application No. PCT/US03/26424.
Korean Office Action dated May 26, 2009, and English translation in a corresponding application owned by the applicants.

(56) References Cited

OTHER PUBLICATIONS

Korean Office Action dated Nov. 23, 2009, and English translation, in applicant's corresponding Korean application No. 10-2006-7003827.
Korean Office Action and its English Translation dated Jun. 22, 2010 from Applicant's Korean Patent Appln. No. 10-2006-7003827, that corresponds to PCT/US2003/026424.
Korean Office Action and its English Translation dated Jul. 6, 2010 in the Assignee's Korean Application No. 10-2004-17013118, that is the Nationalized Appln. from PCT/US03/005521, claiming priority from U.S. Appl. No. 60/358,718.
Korean Patent Office Action dated Sep. 26, 2012, from Korean Patent Application No. 10-2007-7021197 based on PCT/US2006/006422, and its English translation.
Korean Office Action and English Translation dated Jul. 28, 2014 issued in Korean Patent Application No. 10-2009-7023432, 8 pp.
Korean Office Action dated Jan. 16, 2015 from the South Korea Patent Office for applicant's application corresponding to PCT Application No. PCT/US2008/012440.
Mexican Office Action dated Feb. 23, 2009 in a corresponding application owned by the applicants in Mexican Patent Appln. No. PA/a/2004/008253.
Mexican Office Action dated May 2010, and its English translation of rejected parts of the Office Action, from Mexican Patent Application No. PA/a/2004/008253 corresponding to International Patent Application No. PCT/EP2003/005521.
Mexican Office Action and its English translation dated Oct. 20, 2011.
Mexican Office Action dated Aug. 27, 2012, corresponding to U.S. Appl. No. 12/081,236, filed Apr. 11, 2008 (No Translation).
New Zealand Examination Report dated Jan. 8, 2008 from corresponding New Zealand Patent Office.
New Zealand Examination Report dated Oct. 6, 2008 issued by the New Zealand Patent Office in one of Applicants' corresponding foreign applications.
New Zealand Examination Report dated Jul. 2, 2009 issued by the New Zealand Patent Office in one of Applicants' corresponding foreign applications.
New Zealand Examination Report dated Apr. 7, 2010 issued by the New Zealand Patent Office in Applicants' corresponding foreign Application No. 584433.
New Zealand Examination Report dated Oct. 7, 2010 issued by the New Zealand Patent Office in one of Applicants' corresponding foreign applications.
New Zealand Examination Report dated Jan. 21, 2011.
New Zealand Examination Report dated Oct. 2011 issued by the New Zealand Patent Office in Applicants' corresponding foreign Application No. 595624.
Norwegian Office Action and its English Translation dated Jun. 22, 2010 in the Assignee's Norwegian application relating to PCT/US2003/005521.
Norwegian Office Action and its English Translation dated Feb. 16, 2011, from Norway Patent Application No. 20043661, based on International Patent Application No. PCT/US2008/012440.
Polish Office Action dated Feb. 23, 2010 from Polish Patent Application No. P-373780 based on PCT/US2003/005521.
Polish Office Action dated Sep. 2010 in corresponding Polish Application No. P-373780.
Ukraine Office Action dated Aug. 2010 (No English translation.).
U.S. Final Office Action dated Dec. 4, 2008 from U.S. Appl. No. 11/361,054, 6 pages.
U.S. Non-Final Office Action dated Aug. 24, 2007, in U.S. Appl. No. 11/790,779, 6 pages.
U.S. Non-Final Office Action dated Sep. 28, 2007, in U.S. Appl. No. 11/723,383, 5 pages.
U.S. Non-Final Office Action dated Nov. 13, 2008, in U.S. Appl. No. 10/647,132, 7 pages.
U.S. Non-Final Office Action dated Oct. 28, 2009, in U.S. Appl. No. 11/361,054, 5 pages.
U.S. Non-Final Office Action dated Sep. 22, 2011, in U.S. Appl. No. 11/790,779, 8 pages.
U.S. Non-Final Office Action dated Dec. 19, 2011 in U.S. Appl. No. 12/801,726, 7 pages.
U.S. Non-Final Office Action dated Jan. 4, 2012 in U.S. Appl. No. 13/137,337, 5 pages.
U.S. Non-Final Office Action dated Jan. 24, 2012 in U.S. Appl. No. 13/137,322, 9 pages.
U.S. Non-Final Office Action dated Mar. 16, 2012 in U.S. Appl. No. 13/137,324, 5 pages.
U.S. Non-Final Office Action dated May 10, 2012 in U.S. Appl. No. 13/067,469, 17 pages.
U.S. Final Office Action dated Jul. 26, 2012 in U.S. Appl. No. 12/801,726, 6 pages.
U.S. Non-Final Office Action dated Sep. 6, 2012 in U.S. Appl. No. 13/137,322, 9 pages.
U.S. Final Office Action dated Sep. 18, 2012 in U.S. Appl. No. 13/137,337, 5 pages.
U.S. Final Office Action dated Dec. 24, 2012 in U.S. Appl. No. 13/137,324, 10 pages.
U.S. Final Office Action dated Jan. 15, 2013 from U.S. Appl. No. 13/067,469, 21 pages.
U.S. Final Office Action dated Apr. 5, 2013 from U.S. Appl. No. 13/137,322, 10 pages.
U.S. Final Office Action dated Jun. 12, 2013 from U.S. Appl. No. 12/801,726, 6 pages.
U.S. Advisory Office Action dated Jul. 16, 2013 in U.S. Appl. No. 13/137,324, 7 pages.
U.S. Non-Final Office Action dated Jul. 29, 2013 from U.S. Appl. No. 13/067,469, 21 pages.
U.S. Non-Final Office Action dated Aug. 22, 2013 from U.S. Appl. No. 13/507,365, 6 pages.
U.S. Final Office Action dated Nov. 20, 2013 in U.S. Appl. No. 13/137,337, 5 pages.
U.S. Non-Final Office Action dated Dec. 6, 2013 from U.S. Appl. No. 13/137,322, 8 pages.
U.S. Non-Final Office Action dated Jan. 30, 2014 from U.S. Appl. No. 12/801,726, 5 pages.
U.S. Final Office Action dated May 8, 2014 from U.S. Appl. No. 13/507,365, 5 pages.
U.S. Non-Final Office Action dated Jun. 5, 2014 from U.S. Appl. No. 13/067,469, 26 pages, Gainer.
U.S. Non-Final Office Action dated Jun. 9, 2014 from U.S. Appl. No. 13/137,324, 7 pages, Gainer et al [4112-122].
U.S. Non-Final Office Action dated Jun. 26, 2014 in U.S. Appl. No. 13/137,337, 5 pages.
U.S. Final Office Action dated Sep. 8, 2014 issued in U.S. Appl. No. 12/801,726, 23 pages.
U.S. Non-Final Office Action dated Oct. 1, 2014 issued in U.S. Appl. No. 13/621,650, 51 pages.
U.S. Final Office Action dated Nov. 25, 2014 in U.S. Appl. No. 13/067,469, 13 pages.
U.S. Non-Final Office Action dated Dec. 8, 2014 in U.S. Appl. No. 13/137,324, 11 pages.
U.S. Non-Final Office Action dated Dec. 29, 2014 in U.S. Appl. No. 13/507,365, 5 pages.
6th Notification of Office Action dated Aug. 16, 2016, issued in Chinese Patent Application No. 200880114310.9, which is the national phase of PCT/US2008/012440, and English translation.
Galinski, Erwin A., et al., "The Kosmotropic (Structure-Forming) Effect of Compensatory Solutes," Comp. Biochem. Physiol., vol. 117A, No. 3, 1997, pp. 357-365.
Lever, M., et al., "Some ways of looking at compensatory kosmotropes and different water environments," Comparative Biochemistry and Physiology, Part A, vol. 130, 2001, pp. 471-486.
Stennett, Amanda K., et al., "trans-Sodium Crocetinate and Diffusion Enhancement," J. Phys. Chem. B, vol. 110, No. 37, 2006, pp. 18078-18080.
Decision for Rejection dated Nov. 28, 2016, issued in Chinese Patent Application No. 201180033875.6, which is a national phase of PCT/US2011/000997, and English translation.

(56) References Cited

OTHER PUBLICATIONS

Re, Roberta, et al., "Isomerization of Lycopene in the Gastric Milieu," Biochemical and Biophysical Research Communications, vol. 281, No. 2, 2001, pp. 576-581.

* cited by examiner

Figure 1. Mean TSC plasma concentration following administration of 2.9 mg/kg TSC directly to the(●) ileum (*in-situ* dosing) and (○)stomach.

Figure 2: Effect of g-cyclodextrin on TSC absorption in the jejunum of the rat.

Fig. 4

Figure 4: Effect of TSC dosage in a TSC-γ-cyclodextrin mixture on Cmax.

ORAL FORMULATIONS OF BIPOLAR TRANS CAROTENOIDS

This application is a continuation application that claims priority from U.S. patent application Ser. No. 13/067,469, filed on Jun. 2, 2011, which claims priority from U.S. provisional patent application No. 61/350,804, filed on Jun. 2, 2010, the entire contents of which are hereby incorporated by reference.

The subject invention relates to formulations of diffusion enhancing compounds. The compositions of the subject invention typically include a bipolar trans carotenoid, a cyclodextrin and a coating. Included are compositions that are enterically coated with a pH responsive compound for oral delivery.

BACKGROUND OF THE INVENTION

Peroral delivery of therapeutics is generally considered to be the most popular method of drug delivery for patients since this route, in general, increases patient compliance, decreases the number of side effects associated with injections, and provides convenience for the user. Such an administration route is greatly favored for dosing chronically ill patients.

Carotenoids are a class of hydrocarbons consisting of isoprenoid units. The backbone of the molecule consists of conjugated carbon-carbon double and single bonds, and can also have pendant groups. Crocetin and trans sodium crocetinate (TSC) are known to increase the diffusivity of oxygen in aqueous solutions.

U.S. Pat. No. 6,060,511 relates to trans sodium crocetinate (TSC) and its uses. The patent covers various uses of TSC such as improving oxygen diffusivity and treatment of hemorrhagic shock.

U.S. patent application Ser. No. 10/647,132 relates to synthesis methods for making bipolar trans carotenoid salts (BTC) and methods of using them.

U.S. patent application Ser. No. 11/361,054 relates to improved BTC synthesis methods and novel uses of the BTC.

U.S. patent application Ser. No. 12/081,236 relates to the use of bipolar trans carotenoids as a pretreatment and in the treatment of peripheral vascular disease.

U.S. patent application Ser. No. 12/289,713 relates to a new class of therapeutics that enhance small molecule diffusion.

U.S. Provisional Application Ser. No. 61/213,575 relates to the use of diffusion enhancing compounds with thrombolytics.

A variety of bipolar trans carotenoids formulations have been disclosed. See commonly owned application U.S. patent application Ser. No. 10/647,132 and U.S. patent application Ser. No. 11/361,054.

SUMMARY OF THE INVENTION

The pharmaceutical compositions of the subject invention include a diffusion enhancing compound, a cyclodextrin and a coating. The invention also relates to methods of forming a pharmaceutical composition for oral delivery of a bipolar trans carotenoid comprising mixing a bipolar trans carotenoid with a cyclodextrin, adding the mixture to a capsule or making a tablet, and adding coating, advantageously, an enteric coating. Also included in the invention are methods of increasing the diffusivity of oxygen in a mammal and methods of treating a mammal having a disease or condition characterized by hypoxia such as ischemia, cancer, traumatic brain injury, respiratory disease, hemorrhagic shock, cardiovascular disease, multiple organ failure, atherosclerosis, PAD, PVD, myocardial infarction, emphysema, asthma, ALI, ARDS, COPD, hypertension, cerebral edema, papillomas, spinal cord injury, conditions of the central nervous system particularly diseases characterized by neuro-degeneration, and metabolic syndrome and its complications.

DETAILED DESCRIPTION OF THE INVENTION

Although a bipolar trans carotenoid (BTC) such as trans sodium crocetinate (TSC), is a member of the carotenoid family of compounds, it cannot be orally dosed in a manner similar to other carotenoids which are sold in capsule or pill form (e.g., beta carotene or Vitamin A). Two factors which must be accounted for in developing an oral formulation of a BTC compound are pH and solubility considerations which are totally different from other carotenoid compounds. Methods used for formulation of other carotenoid compounds simply don't work for compounds such as TSC.

TSC is precipitated under acidic conditions, such as those which exist in the stomach. This solid material is practically insoluble in the acidic environment of the stomach. TSC is not stable in acidic conditions and will be converted to the cis isomer which can precipitate. A system has been devised that will protect TSC in the harsh, acidic environment of the stomach and release TSC in a more favorable pH region. A more favorable pH does exist in the small intestines. In-situ closed loop studies have shown increased bioavailability when TSC is administered directly to the small intestine compared to the stomach. See Examples below. TSC's effectiveness is believed to be dependant on the TSC concentrations levels found in the body. The effectiveness of TSC can be prolonged by administering TSC orally.

Tablets of bipolar trans carotenoids include excipients that are commonly used in making tablets. Advantageously, tablets also have an enteric coating placed on them, so that they will dissolve in the higher pH (>5.5) areas of the digestive track instead of in the acidic stomach.

Figure 3:
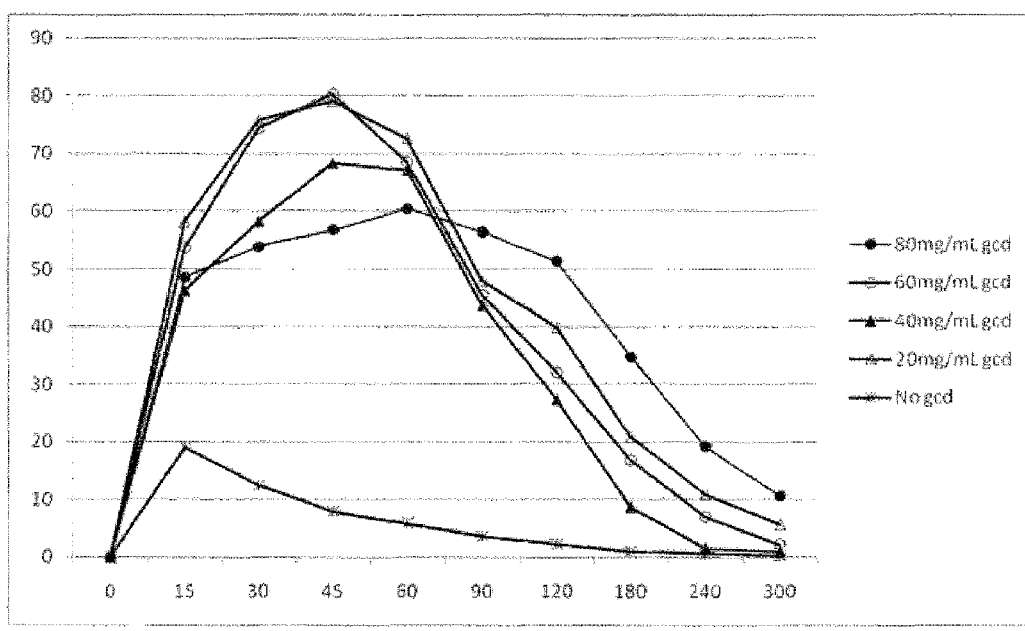

The FIG. 3 graph is TSC plasma concentration versus time following administration.

FIG. 4 shows the effect of TSC dosage in a TSC-γ-cyclodextrin mixture on Cmax.

Figure 5:
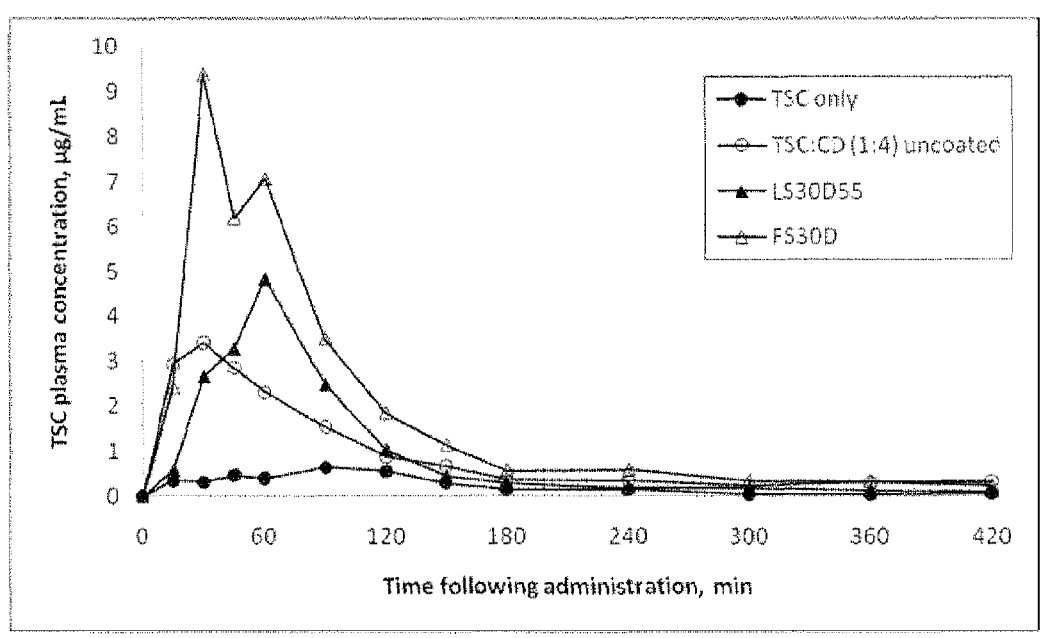

FIG. 5 shows the concentration in the blood stream after oral administration to rats.

Figure 6:
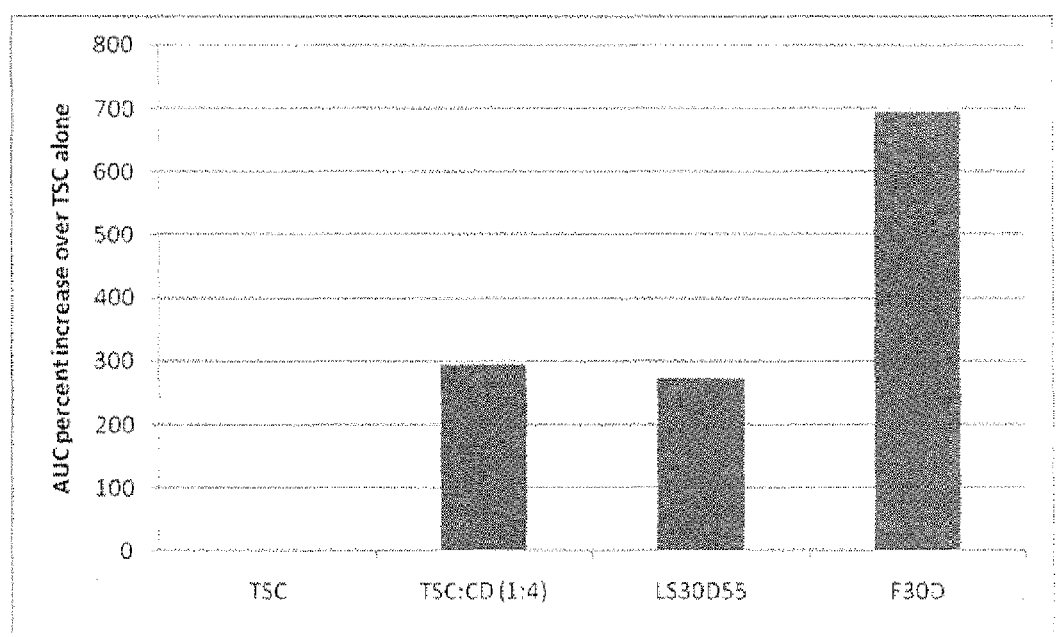

FIG. 6 shows the percentage improvement in absorption.

Figure 7:
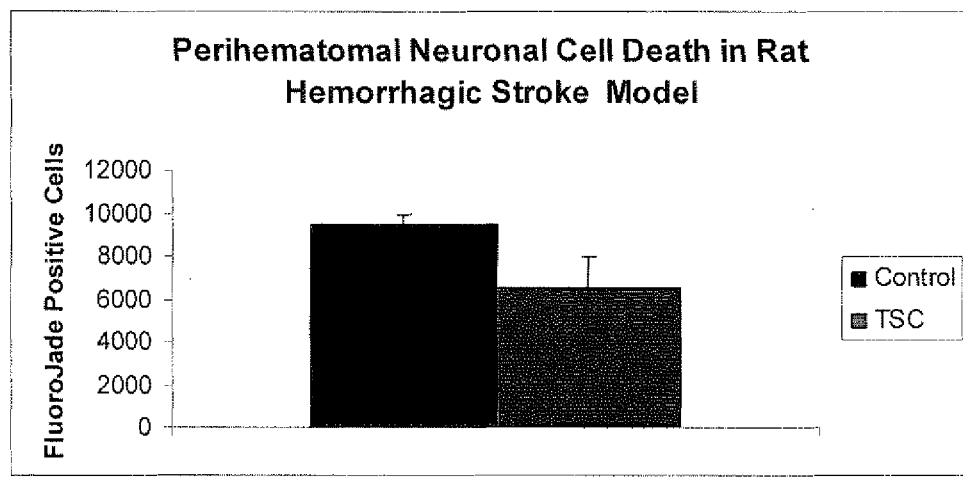

FIG. 7 shows less neuronal death in animals treated with TSC.

Figure 8:
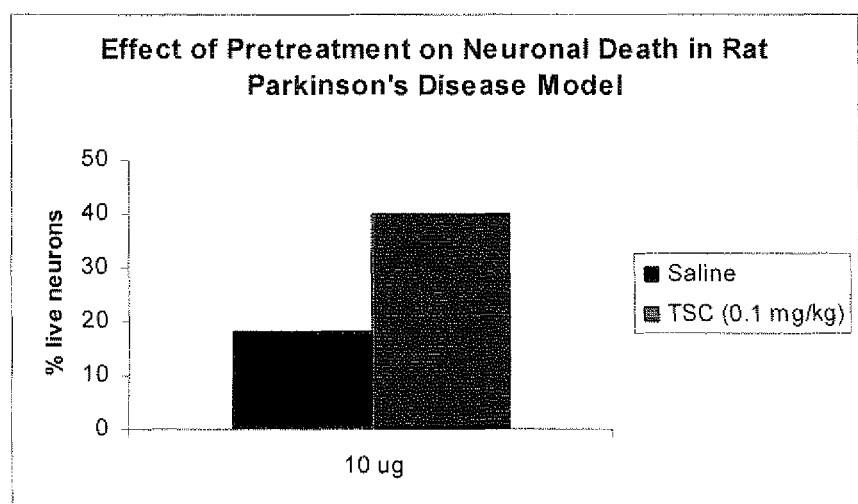

FIG. 8 shows the effect of TSC pretreatment on neuronal death in rats.

Figure 9:
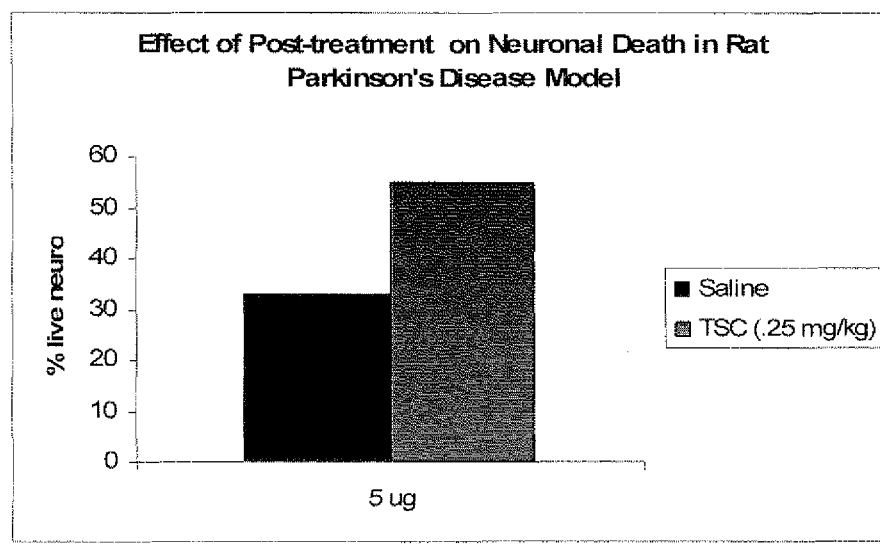

FIG. 9 shows the effect of TSC post-treatment on neuronal death in rats.

Figure 10:
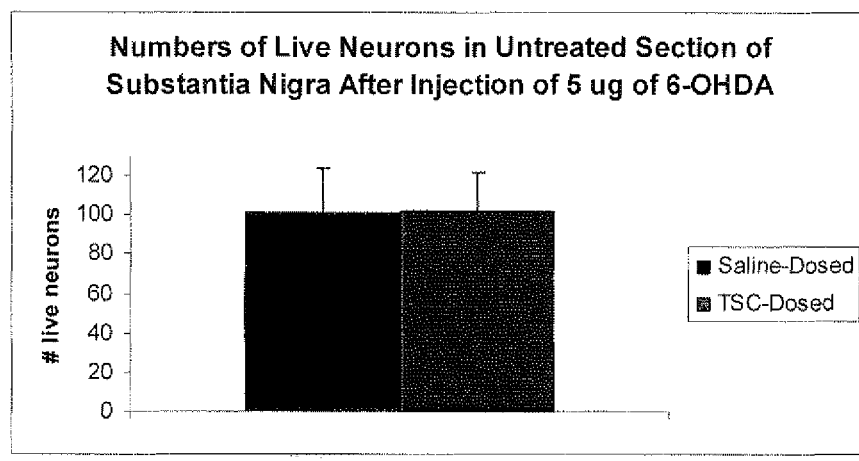

FIG. 10 shows that TSC has no effect on the viability of live neurons.

Figure 11:
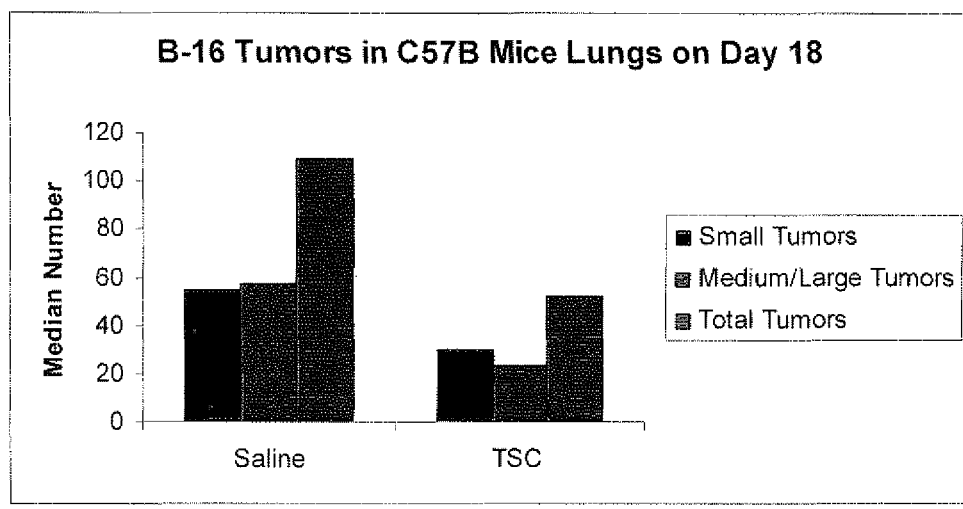

FIG. 11 shows data on B-16 Tumors in C57B Mice Lungs on Day 18 (median values).

Figure 12:
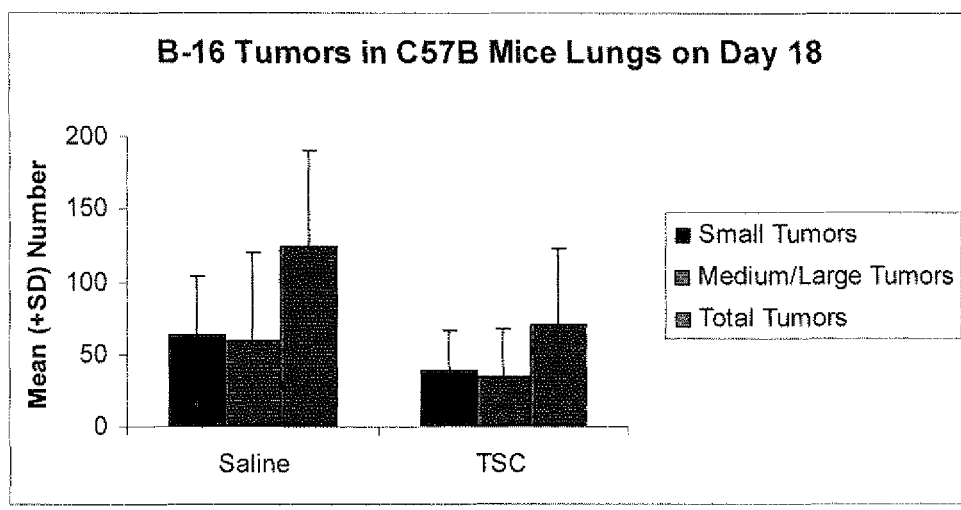

FIG. 12 shows data on B-16 Tumors in C57B Mice Lungs on Day 18 (mean values).

COMPOSITIONS OF THE INVENTION

The compositions of the subject invention are all manufactured to be pharmaceutical grade, i.e. pharmaceutical compositions. Such formulations can include pharmaceutically acceptable carriers known to those skilled in the art as well as other therapeutic agents. Advantageously, the formulation does not include a compound that inhibits the ability of the diffusing enhancing compound to improve diffusivity.

The compositions of the subject invention include a) a diffusion enhancing compound, b) a cyclodextrin and c) a coating. As an alternative, a pH responsive carrier (i.e. TSC is dispersed/held in a polymer matrix), or a time release system (also known as sustained release, controlled, etc.) can be used.

A. Diffusion Enhancing Compounds

The diffusion enhancing compounds of the invention include those compounds described in U.S. Ser. No. 10/647,132, U.S. Ser. No. 11/361,054, U.S. Ser. No. 12/081,236 and U.S. Ser. No. 12/289,713, each of which is hereby incorporated by reference in its entirety.

The diffusion enhancing compounds of the subject invention are trans carotenoids including trans carotenoid diesters, dialcohols, diketones and diacids, bipolar trans carotenoids (BTC), and bipolar trans carotenoid salts (BTCS). Included are bipolar trans carotenoid compounds having the formula:

where:
Y=a cation
Z=a polar group which is associated with the cation, and
TCRO=trans carotenoid skeleton,
such as TSC.
More specifically:
Y (which can be the same or different at the two ends) =H or a cation other than H, preferably $Na^+$ or $K^+$ or $Li^+$.
Y is
advantageously a monovalent metal ion. Y can also be an organic cation, e. g., $R_4N^+$, $R_3S^+$, where R is H, or $C_nH_{2n+1}$ where n is 1-10, advantageously 1-6. For example, R can be methyl, ethyl, propyl or butyl.
Z (which can be the same or different at the two ends)= polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $C_nH_{2n+1}$.
TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group ($CH_3$), an ethyl group ($C_2H_5$), a phenyl or single aromatic ring structure with or without pendant groups from the ring, a halogen-containing alkyl group (C1-C10) such as $CH_2Cl$, or a halogen such as Cl or Br or a methoxy ($OCH_3$) or ethoxy ($OCH_2CH_3$). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbance of the highest peak occurs in the visible wave length range of 380 to 470 nm (the number depending on the solvent used and the chain length of the BTC or BTCS). The addition of pendant groups or differing chain lengths may change this peak absorbance but someone skilled in the art will recognize the existence of an absorbance peak in the visible range corresponding to the conjugated backbone structure of these molecules, divided by the absorbency of the peak which occurs in the UV wave length range of 220 to 300 nm, can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm. According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis on the synthetic TSC as described in U.S. Ser. No. 10/647,132 and U.S. Ser. No. 11/361,054, that ratio is greater than 7.0 (e.g. 7.0 to 8.5), advantageously greater than 7.5 (e.g. 7.5-8.5), most advantageously greater than 8. The synthesized material is a "purer" or highly purified trans isomer.

Advantageously, the trans carotenoid is crocetin, crocin, a bipolar trans carotenoid (BTC) salt such as TSC, or a carotenoid diester, alcohol or acid.

B. Cyclodextrins

Many excipients have been suggested to increase bioavailability of drugs from the gastrointestinal tract such as surfactants, chelating agents, glycols, polyethylene glycol and others; however, cyclodextrin with a bipolar trans carotenoid works extremely well.

A detailed description of cyclodextrins in combination with bipolar trans carotenoids can be found in commonly owned application U.S. Ser. No. 11/361,054 which is hereby incorporated by reference in its entirety.

Advantageously, the bipolar trans carotenoid is in the form of a composition comprising a trans carotenoid and a cyclodextrin, for example alpha cyclodextrin, beta cyclodextrin or gamma cyclodextrin. The cyclodextrin can be hydroxylpropyl-beta-cyclodextrin or 2-hydroxylpropyl-gamma-cyclodextrin. In another embodiment, the composition further comprises mannitol or saline. In a still further embodiment, the composition further comprises a compound to regulate pH such as bicarbonate or glycine. Advantageously, the ratio of a bipolar trans carotenoid to the cyclodextrin is up to 1:10. Advantageously, up to 1:4, e.g. 2:1, 1:1, or 1:4.

C. Coatings

An enteric coating is a barrier applied to oral medication that controls the location in the digestive system where it is absorbed. Enteric refers to the small intestine, therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH of 1 to 3), but they will in the higher pH(above pH 5.5) environment present in the small intestine. Materials used for enteric coatings include fatty acids, waxes, and shellac as well as plastics.

Bipolar trans carotenoids precipitate in acid conditions. For such types of drugs, an enteric coating can be added to the formulation to protect the active substance from the stomach's acidic exposure, delivering the active instead to a basic pH environment (intestine's pH 5.5 and above) where it is more soluble, and can give its desired action.

TSC's effectiveness is believed to be dependent on the TSC concentrations levels found in the body. The effectiveness of TSC can be prolonged by administering TSC orally. Since TSC precipitates in acidic conditions, the compositions of the subject invention protect TSC in the harsh, acidic environment of the stomach and release TSC in a more favorable pH region in the intestines.

An enteric coating is applied to oral dosage formulations in order to protect the active substance from dissolution in the gastric fluid within the stomach. The most common reasons for using an enteric coating include:

Protection of the active substance from the gastric enzymes or acidity of the gastric fluid
Masking of the task or odor
Preventing irritation of the stomach including nausea and vomiting
Sustained release for controlled absorption
Delivery of the active substance to a specific site in the digestive tract that is more favorable for systemic absorption Another embodiment includes using an enteric coating that responds at a broader range of pH values in order to allow a bipolar trans carotenoid such as TSC to absorb in more sections of the intestines, thus increasing the surface area available for absorption.

Composition of Coatings

There are many materials available that are used to enterically coat materials. Most function by either a slow erosion of the coating material (carnauba wax, keratin, gluten, etc.) or by a pH responsive coating. Materials relying on the erosion mechanism are dependent on gastric emptying times. The second type, the pH responsive coating, are hydrophobic and water insoluble at low pH conditions and become soluble at higher pHs. Thus, the coating is insoluble at the harsh acidic environment of the stomach and dissolves at the higher pH region of the intestine. There are many pH sensitive polymers available which can be selected based on a specific pH at which disintegration should occur. The table below lists some of the most common pH sensitive polymers.

Common pH Sensitive Polymers Used for Enteric Coatings

Cellulose acetate phthalate (CAP)
Cellulose acetate succinate
Acrylate polymers
Hydroxy propyl methyl cellulose phthalate
Hydroxy propyl methyl cellulose acetate succinate
Polyvinyl acetate phthalate Three commercially available acrylate polymers—copolymers derived from esters of acrylic and methacrylic acid are Eudragit L30D-55, L100, and FS30D. The pH-dependent functionality of these polymers are determined by their functional, carboxylic acid groups:

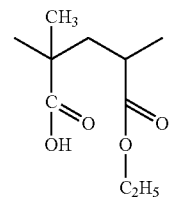

Eudragit L30D-55: Dissolution occurs at a pH of 5.5 or greater with a targeted release area of the duodenum.

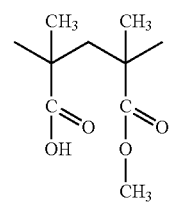

Eudragit L100: Dissolution occurs at a pH above 6.0 with a targeted release area of the jejunum.

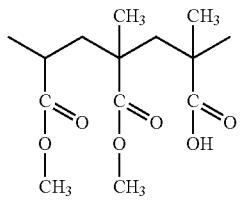 [SMILES: COC(=O)C(C)CC(C)(CC(C)(C)C(=O)O)C(=O)OC]

Eudragit FS30D: Dissolution occurs at a pH above 7.0 with a targeted release area of the colon.

D. Other Ingredients

Agents can be added to buffer the diffusion enhancing compounds. Other agents can be added to affect the osmolality, or added as compounding agents needed for oral formulations. Specific buffering agents include glycine, sodium carbonate, sodium bicarbonate, magnesium carbonate, and aluminum hydroxide. Specific agents to affect osmolality include mannitol, and polysaccharides.

Other agents that can be added include:

Prosolv 90 is a silicified microcrystalline cellulose. The PROSOLV SMCC 90 is said to offer a balance of best in class compaction and flow for tablet formulations. It improves formulation flow, enhances consolidation of the particles, and improves content uniformity.

Crospovidone XL 90 is a cross-linked polyvinylpyrrolidone which is used in tableting as a spheronization aid and an alternative to microcrystalline cellulose. Spheronization, marmumerization, pelletization and micropelletization all mean the same thing: the manufacture of products in small spheres for use in pharmaceutical and related industries. All the products produced by these processes can be called spheroids, spheres, micro-spheres, pellets, micro-pellets or pharmaceutical pellets. All these terms refer to the same thing. Size range is normally from about 0.8 mm to 1.5 mm in diameter although smaller and larger are possible. In contrast, the term granulation normally refers to irregularly shaped particles with a large size range within a batch. Granulated materials are generally less dense.

Magnesium stearate, also called octadecanoic acid, magnesium salt, is a white substance which is solid at room temperature. It has the chemical formula $C_{36}H_{70}MgO_4$. It is a salt containing two equivalents of stearate (the anion of stearic acid) and one magnesium cation (Me).

Magnesium stearate melts at about 88° C., is not soluble in water, and is generally considered safe for human consumption. Because it is widely regarded as harmless, it is often used as a filling agent in the manufacture of medical tablets and capsules. In this regard, the substance is also useful because it has lubricating properties, preventing ingredients from sticking to manufacturing equipment during the compression of chemical powders into solid tablets.

Kollidon is a polyvinyl polymer of variable molecular weight; used as a suspending and dispersing agent and vehicle for pharmaceuticals.

Methods of Formulation

Formulations of the present invention suitable for oral administration can be presented as discrete units such as pills, capsules, cachets or tablets, as powder or granules, or as a solution, suspension or emulsion. Formulations suitable for oral administration further include lozenges, and pastilles. The formulations can conveniently be presented in unit dosage form, and can be prepared by methods known in the art of pharmacy. The formulation can be for immediate, or slow or controlled release of the diffusion enhancing compound. The advantages of a sustained release system (also known as time release, controlled release, etc.) are that dosing frequency can decrease and the systemic drug concentrations are steadier for a longer duration as compared to other formulations of the same drug.

Appropriate dosages of the compositions of the invention will depend on the metabolism of the given compound, and the severity of the condition being treated. For a dose to be "therapeutically effective", it must have the desired effect, i.e. it must relieve symptoms of the indication for which it is given. The therapeutically effective dosage will depend upon the condition treated, the severity of the condition, the stage and individual characteristics of each mammalian patient addressed, and the clearance of the diffusion enhancing effect.

Typically the compositions of the invention are made by mixing the bipolar trans carotenoid and the selected cyclodextrin at a ratio of up to 1:10. Mixing is done by any pharmaceutically accepted method. The mixture is then either loaded into a capsule container or stamped into a tablet (which also can contain the ingredients mentioned previously to promote release from the molds, etc.). The capsules or tablets are then coated by pH-sensitive polymer such as a Eudragit in such a manner so as to create a continuous coating.

In one embodiment of the invention, multiple types of enterically coated beads are placed in a capsule or other system for oral delivery. The beads are composed of a first portion or group of beads having a first coating and a second portion or group of beads having a second coating. Additional groups of beads with different coatings can also be added. An example is a capsule containing beads having three different types of Eudragit coatings that release at different pH values and release over a longer period of time than a capsule containing only one type of bead.

Therapeutic Uses and Modes of Administration

The compositions of the invention have therapeutic uses in treating mammals having tissues experiencing low oxygen levels (hypoxia) or in various conditions involving the central nervous system.

The uses of the compositions of the invention include those disclosed in commonly owned U.S. Pat. No. 6,060, 511, U.S. patent application Ser. No. 10/647,132, U.S. patent application Ser. No. 11/361,054, U.S. patent application Ser. No. 12/081,236 and U.S. provisional Patent application Ser. No. 61/213,575, each of which is hereby incorporated by reference in its entirety.

The oral compositions of the invention are useful in the treatment of:

hemorrhagic shock, respiratory disease, asthma, emphysema, ALI, ARDS, COPD ischemia, cardiovascular disease, atherosclerosis, myocardial infarction, hypertension, ventricular fibrillation stroke, traumatic brain injury, cerebral edema, conditions of the central nervous system (Alzheimer's disease, Parkinson's disease, and other neurodegenerative diseases) Neurodegeneration is the umbrella term for the progressive loss of structure or function of neurons, including death of neurons. Examples of degenerative nerve diseases include: Alzheimer's disease, Parkinson's disease, amyotrophic lateral sclerosis, Friedreich's ataxia, Huntington's disease, Lewy body disease, and spinal muscular atrophy. See Example 7.

arthritis,
anemia, (anemia of prematurity, Fanconi anemia, hymolytic anemia, microcytic anemia, a normochromic anemia, a macrocytic anemia, hereditary spherocytosis, sickle-cell anemia, warm autoimmune hemolytic anemia, cold agglutinin hemolytic anemia),
chronic renal failure, hypertension,
papillomas, spinal cord injuries,
cancer (advantageously as an adjunct to i) radiation therapy including external beam radiation, gamma knife, brachytherapy, tomotherapy, and proton beam, including fractionated, 3D conformal radiotherapy, intracavitary radiation, and intensity modulated radiotherapy (IMRT), and/or ii) chemotherapy including temozolimide).
diabetes, diabetic retinopathy,
peripheral vascular disease/claudication, embolism, blood clot, spinal stenosis/neurogenic claudication,
diseases where organs do not get enough oxygen such as Wegener's granulomatosis The compositions of the invention are also useful as a pretreatment or for treating mammals at risk for the above-noted diseases/conditions.

The compositions are also useful in neuroprotection, i.e. in preventing or delaying the complications associated with neurodegenerative disorders such as Parkinsons disease or Alzheimers disease. They are also useful in reducing the amount of ischemia resulting from surgery in a mammal by administering the composition before during or after surgery The compositions are also useful in enhancing performance when respiration/exertion is increased or stressed, in increasing aerobic metabolism, and in increasing endurance during physical activity such as running walking or lifting.

For the following uses, the diffusion enhancing compounds are administered by any suitable route including oral, nasal or inhalation, topical, parenteral (including subcutaneous, intramuscular, intravenous, intradermal, transdermal and intraosseus), vaginal or rectal. The preferred route of administration will depend on the circumstances. An inhalation route, or intravenous or intramuscular injection is advantageous for treatment in emergency situations, where it is necessary for the diffusion enhancing compound to enter the bloodstream very quickly. In one embodiment, a composition of a cyclodextrin and bipolar trans carotenoid dissolved in sterile water can be injected, either intramuscularly (IM) or intravenously (IV). The formulations thus include those suitable for administration through such routes (liquid or powder to be nebulized). It will be appreciated that the preferred route may vary, for example, with the condition and age of the patient.
critical limb ischemia
Parkinson's disease, amyotrophic lateral sclerosis, Friedreich's ataxia, Huntington's disease, Lewy body disease, and spinal muscular atrophy,
multiple sclerosis,
metabolic syndrome
peripheral neuropathy
cerebral palsy
cancer—a bipolar trans carotenoid salt, such as TSC, is the chemotherapy used to cause regression of many types of cancerous tumors, i.e. without use of radiation or other chemotherapy. Example 8 relates to treating cancerous tumors with TSC. TSC does not work by killing the cancer cells, but, while not wishing to be bound by theory, is thought to work by causing the cells to revert to more mature (and thus, more nearly normal) cells. The use of retinoids (such as all trans retinoic acid), or their salts, for the treatment of cancer is excluded from the invention. Examples of the types of cancer/tumors which can be treated are: skin, lung, breast, brain, bladder, prostate and colon cancers/tumors.

In one embodiment, more than one diffusion enhancing compound is administered. Alternatively, hemoglobins or fluorocarbons and a diffusion enhancing compound can be given together.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Tablet Composition (without Cyclodextrin)
Two formulations were made that consist of the following ingredients:
65% Blend
  65.0% TSC
  26.0% Prosolv 90
  2.9% Crospovidone XL 90
  1.5% Magnesium Stearate
  4.6% Kollidon
60% Blend
  60.4% TSC
  30.1% Prosolv 90
  3.8% Crospovidone XL 90
  1.4% Magnesium Stearate
  4.3% Kollidon The TSC tablets were made in three (3) steps:

Step 1: A mixture containing 70% TSC, 25% Prosolv 90 and 5% Kollidon 25 were mixed in a bag for 5 minutes and roll compacted using a Vector roller compactor. The conditions for the roller compactor were roll pressure=800 psi, screw speed=10 rpm, roll speed=0.95 rpm. This produced a blend called TSC Blend I.

Step 2: The TSC Blend I from Step 1 was roll compacted using Crospovidone XL 10 and magnesium stearate. The percentages were 97.5% TSC Blend I, 2% Crospovidone XL 10 and 0.5% magnesium stearate. The product of this step is called TSC Granules II.

Step 3: The ribbons from Step 2 were hand crushed and sieved through 20 mesh screen. The granules obtained were mixed with excipients (see below) to get final blends containing 65% TSC and 60% TSC.

| 65% TSC Blend | 60% TSC Blend |
| --- | --- |
| 95.2% TSC Granules II | 88.5% TSC Granules II |
| 2.8% Prosolv 90 | 8.5% Prosolv 90 |
| 1% Crospovidone XL | 2% Crospovidone XL |
| 1% Magnesium Stearate | 1% Magnesium Stearate |

Step 4: The tablets were coated with CAP (cellulose acetate phthalate)

To demonstrate the difference in absorption in the stomach and in the intestine, the following studies were performed.

Example 2

Absorption of TSC Solutions

Male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, animals were placed into one of two groups: administration of a TSC dosage formulation directly into the 1) stomach via gavage; or 2) into an isolated intestinal segment. For dosing into an isolated intestinal segment, a front midline in was made, exposing the abdomen and intestinal segments. In this study, the ileum was isolated and cannulated with PE-50 tubing, then washed with normal 37° C. saline until the washings run clear. The segment was replaced, the abdomen clamped, and the rat was allowed to stabilize for 1 hour. The TSC formulation was then introduced into the isolated segment. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

Figure 1:
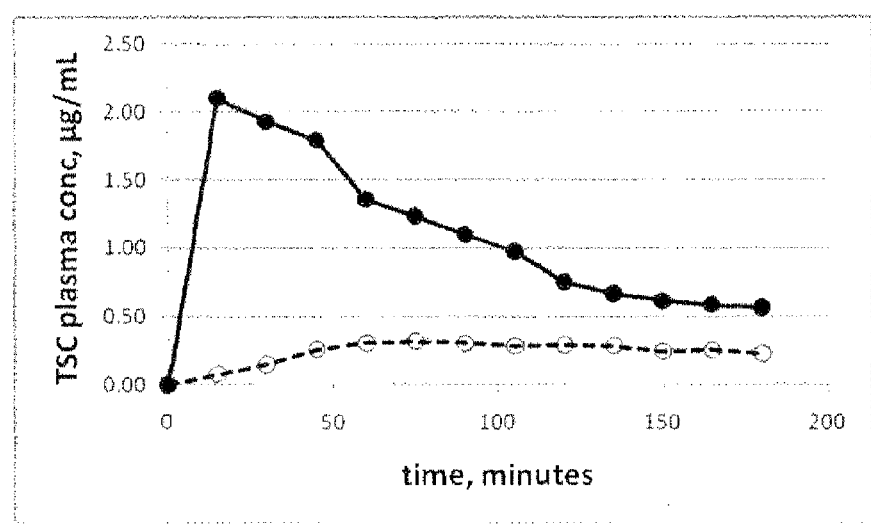
FIG. 1 shows increased bioavailability when TSC is administered directly to the small intestine as compared to the stomach.

The TSC dosage formulation administered in this study consisted of an intravenous formulation (20 mg/mL TSC, 8% gamma cyclodextrin, 50 mM Glycine, and 2.3% Mannitol). FIG. 1 shows that there is an increased bioavailability when TSC is administered directly to the small intestine as compared to the stomach.

Example 3

Enteric Coated Tablets (without Cyclodextrin)

TSC is precipitated and is practically insoluble under the harsh acidic environment of the stomach. TSC must be protected from the harsh environment of the stomach and be release in a more favorable, higher pH region of the small intestine. For this study, tablets of TSC were made (Table 1) and were enterically coated with either Eudragit L100 or cellulose acetate phthalate (CAP). The integrity of both types of protective coatings were confirmed in a USP dissolution study in which enterically coated tablets were first place in a dissolution cell containing simulated gastric fluid (SGF), then transferred to another cell containing simulated intestinal fluid (SIF). The coating and tablet remained intact in the SGF, but dissolution did occur in SIF. This study was performed according to USP protocols.

TABLE 1

TSC tablet formulation

| 65% TSC Blend | 60% TSC Blend |
|---|---|
| 95.2% TSC Granules II | 88.5% TSC Granules II |
| 2.8% Prosolv 90 | 8.5% Prosolv 90 |
| 1% Crospovidone XL | 2% Crospovidone XL |
| 1% Magnesium Stearate | 1% Magnesium Stearate |

These tablets were made using tabletting technology known to one skilled in the art.

Then, in order to examine what happens with enterically-coated TSC, a tablet coated with CAP, and containing 300 mg TSC using the 65% blend, was administered orally to dogs. Very low plasma TSC concentrations were found, suggesting that the bioavailability would be too low for clinical use in this formulation.

Example 4

Intestinal Absorption of TSC and Effect of Cyclodextrin

Additional studies were conducted in order to determine the effect on systemic absorption with the addition of gamma cyclodextrin to the TSC.

Male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, a front midline in was made, exposing the abdomen and intestinal segments. In this study, the jejunum was isolated and the TSC formulation was administered in the proximal jejunum. Approximately 60 mg/kg TSC was administered at various gamma cyclodextrin ratios of 0.5:1 up to 4:1 (wt. TSC:wt. gamma cyclodextrin). Movement of TSC within the intestinal segments was not restricted distal to the site of administration. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

Figure 2:
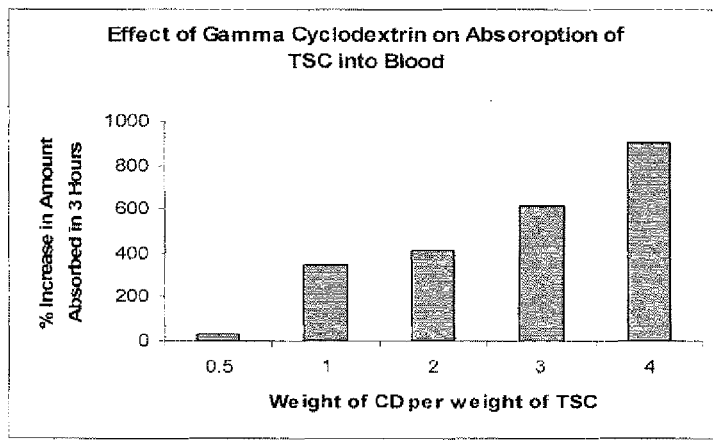
FIG. 2 shows the effect of g-cyclodextrin on TSC absorption in the jejunum of the rat.

It was found that the γ-cyclodextrin greatly enhances the absorption of the TSC as shown in FIG. 2.

FIG. 3 shows the pk curves following in-situ TSC administration into the small intestine. The curves show that cyclodextrin significantly increases intestinal absorption of TSC.

The FIG. 3 graph is TSC plasma concentration (μg/mL) vs. time following administration (min).

Example 5

Scalability for Cmax

It has been found that gamma cyclodextrin greatly enhances the systemic absorption of TSC in the GI tract. The dosage of TSC used in the above study is large, therefore, additional doses of TSC were administered with gamma cyclodextrin at a ratio of 1:1 (wt. TSC:wt. gamma cyclodextrin) in order to determine the scalability of systemic absorption (in terms of Cmax) with respect to TSC dosing amount. For the following study, TSC was administered to the jejunum intestinal segment at the following dosages: 2.5, 5, 10, and 60 mg/kg.

For this study, male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, a front midline in was made, exposing the abdomen and intestinal segments. In this study, the jejunum was isolated and the TSC formulation was administered in the proximal jejunum. Movement of TSC within the intestinal segments was not restricted distal to the site of administration. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

The results are shown in FIG. 4. The line in FIG. 4 is a linear regression of the data, and shows that an excellent fit is obtained. This suggests that the data obtained for the inclusion of γ-cyclodextrin is scalable to other TSC dosages.

Example 6

Intestinal Absorption with and without Enteric Coatings

Additional studies were conducted in order to investigate the benefit of including gamma cyclodextrin with TSC for use in peroral delivery, For this study, TSC and gamma cyclodextrin at a ratio of 1:4 (wt TSC:wt. gamma cyclodextrin) were packed in size 9 gelatin capsules and either: 1) left uncoated, 2) enterically coated with Eudragit L30D-55 (also referred to as LS30D55 herein) (a coating which should disintegrate at a pH greater than 5.5), or 3) enterically coated with Eudragit FS30D (a coating which should disintegrate at a pH greater than 7). Uncoated capsules containing TSC only (without cyclodextrin) were also administered.

For this study, male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

After cannulation, a gelatin capsule contain drug product was administered to the stomach via dosing syringe (Torpac, Fairfield N.J.) followed by 0.3 mL sterile water to the stomach via gavage. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

The graph in FIG. 5 shows the concentration in the blood stream after oral administration to rats over a period of 7 hours of dry powders contained in gelatin capsules, with all capsules containing the same amount of TSC (about 4 mg).

TSC only shows the TSC alone in a capsule;

TSC:CD (1:4) uncoated, which is for capsules made of a 1 to 4 mixture of TSC to cyclodextrin but with no coating applied to the gelatin capsules;

LS30D55 which is for the same 1:4 capsule coated with Eudragit LS30D55 (a coating which should disintegrate at a pH greater than 5.5);

FS30D, which is for the same 1:4 capsule coated with Eudragit FS30D (a coating which should disintegrate at a pH greater than 7).

The bar graph in FIG. 6 shows the percentage improvement in absorption (as compared to TSC only) that is obtained with the uncoated capsules as well as the ones coated with the Eudragits.

Example 7

Neurodegenerative Disease

A major aspect of any neurodegenerative disease is, as stated above, the death of neurons. Studies have been conducted to look at the effects of TSC on neuronal death in different animal models.

The first study in which this was done was one conducted using a rat model of hemorrhagic stroke. For that study, the enzyme collagenase was injected through a burr hole in the skull into the right basal ganglion, which resulted in some of the brain blood vessels rupturing and bleeding out. TSC was then injected starting 3 hours after the collagenase was administered, and the animals were sacrificed 48 hours after the administration of the collagenase.

When there is a hemorrhage in the brain, the blood pools and forms a hematoma. Around the periphery of this hematoma, there is a death of neuronal cells. However, it was found that treating with TSC resulted in about 20% less death of the neurons. Use of the stain, fluorojade, allows one to count the numbers of "dead" neurons in a given brain section of the brain. This was done in the area around the hematomas formed in the hemorrhagic stroke rat model. It was found that there was approximately 30% less neuronal death in the animals treated with TSC as shown in the FIG. 7 graph.

Another model that was used examined the effect of TSC on neuronal viability is a rat model of Parkinson's disease. In this model, a burr hole is drilled through the skull and into the region of the substantia nigra. The Parkinson's-like condition is induced by injecting 6-hydroxydopamine (6-OHDA) into the brain. An amount of 10 □g of 6-OHDA is frequently injected in this model, and was used in the first study.

The first study with this model was designed to mimic a study found in the literature, in which pretreatment with crocetin was found to have a beneficial effect on neuronal death following the injection of 10 □g of 6-OHDA. In the study, TSC was injected at a dosage of 0.1 mg/kg for 7 days preceding the injection of the 6-OHDA (the same dosing regimen as had been done in the crocetin study). Following the injection of the 6-OHDA, no further treatments were given over the next 4 weeks.

At that time the rats were sacrificed and the brains removed and sent to Charles River Laboratories for counts of live neurons. This resulted in counts on the right side of the brain, where the 6-OHDA had been inected, as well as on the untreated left side of the brain. This allowed the comparison of cell death (treated side count/untreated side count) of the controls, which had been pretreated with saline, to the animals pretreated with TSC. The graph FIG. 8 shows these results.

As can be seen, the percentage of live neurons after this treatment is approximately doubled. It should also be noted that this is a very severe model of neuronal death, in that around 85% of the neurons are dead in the controls.

It is of much more interest to know the effect of post-treatment on neuronal death following the injection of 6-OHDA. To investigate that, 5 □g of 6-OHDA were again injected into the substantia nigra as before, but the treatment began following that injection. The animals were then given daily injections of TSC (0.25 mg/kg) for 4 weeks before sacrifice. The brains were removed and sent to Charles River Laboratories for neuronal counts.

As seen in FIG. 9, there are more live neurons (about 20% more) with the TSC treatment, and these data are statistically-significantly different (p<0.05).

An interesting result of this study was that the brain sections of the non-6-OHDA side of the brains showed almost the same numbers of live neurons regardless of whether saline or TSC were injected, as shown in the FIG. 10 graph. This demonstrates that TSC has no effect on the viability of live neurons.

These results, combined with those found in the hemorrhagic stroke model, teach that TSC exerts a neuroprotective effect in the brain.

Example 8

Chemotherapy with TSC

The pulmonary metastasis mouse model is a widely used model for the evaluation of tumor therapy. With B16 (mouse melanoma) cells, essentially all cells "take" upon intravenous cell injection in the tail vein, and the tumors are preferentially formed in the lungs. Thus, the term pulmonary metastasis is widely used even though every resulting pulmonary nodule is technically an independent "primary" tumor rather than a true metastasis.

Since the melanin in B16 cells does not bleach like the rest of the pulmonary tissues, the tumor nodules can be easily visualized after bleaching the extracted lungs in Fekete's solution. There is always a fraction of nodules that is amelanotic ("white") though, and this requires careful counting in order not to underestimate the tumor burden.

For the subject studies, eight-week-old female C57BL/6 mice were obtained from Charles River Laboratories. The mice were housed in groups of 5 or fewer, and received food and water ab libitum.

B16 cells were cultured by the Center for Cell Signaling of the University of Virginia using a standard protocol. The cells were received while they were in an exponential growth phase. The cells were supplied at a concentration of $5 \times 10^5$ cells/mL in Hank's buffered salt solution (HBSS).

The cells were injected immediately upon receipt, and this day was designated as Day 0. On Day 0, all of the mice were injected intravenously in the tail vein with 0.1 mL of the cell suspension, meaning that each mouse received $0.5 \times 10^5$ cells. The mice were then left alone until Day 4.

On Day 4, the mice were divided into two groups: Group A, consisting of 5 mice, received an intravenous injection of 0.05 mL of saline in the tail vein. Group B, composed of 7 mice, received an intravenous injection of 0.05 mL of a TSC solution in the tail vein, for a TSC dosage of 0.142 mg/kg/day. The same injections were repeated on Days 5-8 and on Days 11-15. On Day 18, the mice were sacrificed using carbon dioxide. The lungs were excised, rinsed and placed in Fekete's Solution and stored at room temperature.

Later, the lungs were assessed visually, in random, blinded order, to obtain a visual count of the numbers of tumors. It was found that there was a mixture of small tumors plus medium-sized and larger tumors. Thus, the tumors were counted visually in two separate groups: small tumors and medium/large tumors. Although the majority of the tumors were black, there were also some white tumors.

The results of the tumor counts are shown in the table and in the FIGS. 11-12 graphs. The table shows the median (med.) numbers of each type of tumor group as well as the mean±standard deviation. The FIG. 11 graph shows the median values and the FIG. 12 graph shows the mean values. The groups were not statistically different due to the large standard deviations.

TABLE

| Group | N | Small med. | Small mean | Medium/Large med. | Medium/Large mean | Total med. | Total mean |
|---|---|---|---|---|---|---|---|
| Saline | 5 | 55 | 64 ± 40 | 57 | 60 ± 27 | 109 | 124 ± 66 |
| TSC | 7 | 18 | 32 ± 29 | 19 | 30 ± 24 | 34 | 62 ± 53 |

It will be readily apparent to those skilled in the art that numerous modifications and additions can be made to both the present compounds and compositions, and the related methods without departing from the invention disclosed.

What is claimed is:

1. A pharmaceutical composition for oral administration, wherein the pharmaceutical composition comprises: i) a bipolar trans carotenoid salt having the structure:

YZ—TCRO—ZY where
Y=a cation which can be the same or different,
Z=a polar group which can be the same or different and which is associated with the cation, and
TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen, ii) a cyclodextrin, and iii) a coating that avoids conversion of the bipolar trans carotenoid to a cis isomer under acid conditions in a stomach of the mammal.

2. A pharmaceutical composition in oral dosage form, wherein the pharmaceutical composition comprises:

i) a bipolar trans carotenoid salt having the structure:

YZ—TCRO—ZY where
Y=a cation which can be the same or different,
Z=a polar group which can be the same or different and which is associated with the cation, and
TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen, ii) a cyclodextrin, and iii) a coating that avoids conversion of the bipolar trans carotenoid to a cis isomer under acid conditions in a stomach of the mammal.

3. A pharmaceutical composition as in claim 1 or 2, wherein the bipolar trans carotenoid salt is trans sodium crocetinate TSC.

4. A pharmaceutical composition as in claim 1 or 2, wherein the bipolar trans carotenoid salt is trans sodium crocetinate TSC, the cyclodextrin is gamma cyclodextrin, and the coating is an acrylate polymer.

5. A pharmaceutical composition as in claim 1 or 2, wherein the coating is an enteric coating.

6. A pharmaceutical composition as in claim 1 or 2, wherein the coating is an enteric coating which will release the bipolar trans carotenoid at pH greater than 5.5.

7. A pharmaceutical composition as in claim 1 or 2, wherein the coating is an enteric coating which will release the bipolar trans carotenoid at pH greater than 6.5.

8. A pharmaceutical composition as in claim 1 or 2, wherein the coating is a coating which will release the bipolar trans carotenoid in the intestines.

9. A pharmaceutical composition as in claim 1 or 2, wherein the coating is an acrylate polymer.

10. A pharmaceutical composition as in claim 1 or 2, wherein the cyclodextrin is selected from the group consisting of alpha cyclodextrin, beta cyclodextrin, and gamma cyclodextrin.

11. A pharmaceutical composition as in claim 1 or 2, wherein the bipolar trans carotenoid salt is synthetic trans sodium crocetinate wherein the purity level of the trans isomer in the composition is such that under UV-visible analysis, the absorbency of the highest peak which occurs in the visible wave length range divided by the absorbency of the peak which occurs in the UV wave length range is greater than 7.5.

12. A pharmaceutical composition as in claim 1 or 2, wherein the composition is in unit dosage form.

13. A pharmaceutical composition as in claim 1 or 2, wherein the composition is in the form of a tablet, pill, or capsule.

\* \* \* \* \*